United States Patent
Zhao et al.

(10) Patent No.: US 11,667,717 B2
(45) Date of Patent: Jun. 6, 2023

(54) ANTIBODIES BINDING TO HUMAN IL-4R, PREPARATION METHOD THEREFOR AND USE THEREOF

(71) Applicant: SUNSHINE GUOJIAN PHARMACEUTICAL (SHANGHAI) CO., LTD., Shanghai (CN)

(72) Inventors: Jie Zhao, Shanghai (CN); Liangfeng Jiang, Shanghai (CN); Chen Chen, Shanghai (CN); Huiling Wu, Shanghai (CN); Yuping Huang, Shanghai (CN); Haomin Huang, Shanghai (CN); Zhenping Zhu, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 85 days.

(21) Appl. No.: 17/045,285

(22) PCT Filed: Aug. 20, 2019

(86) PCT No.: PCT/CN2019/101628
§ 371 (c)(1),
(2) Date: Oct. 5, 2020

(87) PCT Pub. No.: WO2020/048312
PCT Pub. Date: Mar. 12, 2020

(65) Prior Publication Data
US 2021/0206861 A1    Jul. 8, 2021

(30) Foreign Application Priority Data

Sep. 4, 2018  (CN) .......................... 201811023880.9

(51) Int. Cl.
C07K 16/28       (2006.01)
A61K 39/00       (2006.01)

(52) U.S. Cl.
CPC .... C07K 16/2866 (2013.01); *A61K 2039/505* (2013.01); *C07K 2317/24* (2013.01); *C07K 2317/565* (2013.01); *C07K 2317/76* (2013.01)

(58) Field of Classification Search
CPC ............ C07K 16/2866; C07K 2317/24; C07K 2317/565; C07K 2317/76; C07K 2317/72; A61K 2039/505
See application file for complete search history.

(56) References Cited

U.S. PATENT DOCUMENTS

2011/0189178 A1* 8/2011 Desjarlais et al. . C07K 16/2887
435/69.6

FOREIGN PATENT DOCUMENTS

| CN | 106232140 A | 12/2016 | |
|---|---|---|---|
| CN | 106267190 A | 1/2017 | |
| CN | 107474134 A | 12/2017 | |
| CN | 108373505 A | 8/2018 | |
| CN | 108409860 A * | 8/2018 | ......... C07K 16/2866 |
| CN | 108409860 A | 8/2018 | |
| WO | 2014031610 A1 | 2/2014 | |
| WO | 2016156588 A1 | 10/2016 | |

OTHER PUBLICATIONS

Beckmann et al., "Monoclonal Antibodies Block Murine IL-4 Receptor Function", (1990), The Journal of Immunology, vol. 144 No. 11, p. 4212-4217. (Year: 1990).*
Yang et al., "Expression and Detection of Recombinant Anti-Interleukin-4 Receptor Single-Chain Body", (2017), Heilongjiang Animal Science and Veterinary Medicine, No. 3, p. 164-167. (Year: 2017).*
International Search Report and Written Opinion for PCT/CN2019/101628, dated Nov. 18, 2019.
Beckmann et al., "Monoclonal antibodies block murine IL-4 receptor function" The Journal of Immunology, 1990, v 144, n 11, p. 4212-4217.
Wu et al., "Effect of prepared mIL-4Rα-EX-TT autovaccine on the asthma mice" Chin Med Biotechnol, 2015, v 10, n 5, p. 398-404.
Yang et al., "Expression and detection of recombinant anti-interleukin-4 receptor single-chain body" Heilongjiang Animal Science and Veterinary Medicine, 2017, n 3, p. 164-167.

* cited by examiner

*Primary Examiner* — Daniel E Kolker
*Assistant Examiner* — Danaya L Middleton
(74) *Attorney, Agent, or Firm* — Greer, Burns & Crain, Ltd.; Gregory P. Einhorn

(57) ABSTRACT

Disclosed are antibodies binding to human IL-4R, having identical variable regions and different constant regions, wherein the variable regions can specifically bind to human IL-4R, and the constant regions affect the activity of the whole antibody through an amino acid site mutation. The above-mentioned antibodies can be used to treat diseases related to IL-4R overexpression, such as atopic dermatitis, asthma, etc., and thus possesses good clinical application prospects.

12 Claims, 9 Drawing Sheets

Specification includes a Sequence Listing.

ANTIBODIES BINDING TO HUMAN IL-4R, PREPARATION METHOD THEREFOR AND USE THEREOF

RELATED APPLICATIONS

This application is a national phase application claiming benefit of priority under 35 U.S.C. § 371 to International (PCT) Patent Application serial number PCT/CN2019/101628, filed Aug. 20, 2019, which claims benefit of priority to Chinese Patent Application No. CN 201811023880.9, filed Sep. 4, 2018. The aforementioned applications are expressly incorporated herein by reference in their entirety and for all purposes.

FIELD OF THE INVENTION

The present invention relates to the field of antibodies, and more particularly, the present invention discloses antibodies that bind to human IL-4R, preparation methods and use thereof.

BACKGROUND OF THE INVENTION

Interleukin-4 receptor (IL-4R) is a heterodimer composed of a chain and γc chain; in which the α chain (IL-4Rα) can specifically bind to interleukin-4 (IL-4), then forms a ternary complex with the γc chain, and transduce IL-4 signals for promoting proliferation and gene transcription activation. Interleukin-13 receptor (IL-13R) is a heterodimer composed of IL-13R+1 chain and IL-4Rα chain; in which IL-13Rα1 can specifically bind to interleukin-13, and then forms a ternary complex with IL-4Rα chain to transduce IL-13 signals for promoting proliferation and gene transcription activation. IL-4 and IL-13 play important roles in the pathogenesis of allergic diseases such as allergic dermatitis and asthma.

DUPIXENT® (Dupilumab) injection is a currently marketed monoclonal antibody drug targeting IL-4Rα chain, co-developed by Regeneron Pharmaceuticals and Sanofi-aventis. Dupilumab is a fully human IG4 monoclonal antibody with a molecular weight of about 147 kDa, and can specifically bind to the IL-4Rα subunit shared by the IL-4 and IL-13 receptor complex, thereby inhibiting inflammation reactions mediated by IL-4 and IL-13 cytokines. Dupilumab was approved by FDA in US, EMA in EU, and PMDA in Japan on Mar. 28, 2017, Sep. 27, 2017, and Jan. 19, 2018, respectively. DUPIXENT® was approved for the treatment of adult patients with moderate-to-severe atopic dermatitis whose disease is not adequately controlled with topical therapies or when those therapies are not advisable, which can be used with or without topical corticosteroids. Two recent phase III trials (Castro M, Corren J. Pavord I D, et at. Dupilumab efficacy and safety in moderate-to-severe uncontrolled asthma [J]. New England Journal of Medicine, 2018; 378:2486-2496, DOI: 10.1056/NEJMoa1804092) showed that the patients treated with dupilumab had a significantly lower rate of severe asthma exacerbation than the patients receiving placebo in the control group, and also had better lung function and asthma control; among the patients with higher eosinophil levels, the benefits were more obvious. Based on the above clinical trial results, the U.S. Food and Drug Administration (FDA) has accepted the supplementary Biologics License Application (sBLA) for dupilumab as an additional maintenance treatment in certain adults and adolescents (aged 12 years and older) with moderate-to-severe asthma.

At present, dupilumab has been approved by the FDA for treatment of atopic dermatitis, and may be approved for treatment of moderate-to-severe asthma in the future. However, there is still an urgent need to develop new, specific, and highly effective drugs targeting IL-4Rα t to fill the gaps in the domestic market for similar drugs, so as to improve the quality of life of people with allergic autoimmune diseases in our country and benefit domestic patients.

SUMMARY OF THE INVENTION

In order to solve the above technical problems, the inventors of the present invention conducted a large number of experiments from antigen immunization, hybridona screening, antibody expression, purifcation to biological activity identification, screened and obtained a murine antibody No. 4-2 that specifically binds to human IL-4R. On this basis, its chimeric antibody 4-2-Chimeric-IgG1, humanized antibodies 4-2-Humanized-IgG1 and 4-2-Humanized-IgG4 were further constructed. Experimental results show that the chimeric antibody 4-2-Chimeric-IgG1, the humanized antibodies 4-2-Humanized-IgG1 and 4-2-Humanized-IgG4 can effectively block the interaction between IL-4 and IL-4R, and have inhibition activity on IL-4-induced TF-1 cell proliferation, CD23 expression and IgE secretion on human peripheral blood mononuclear cells (PBMC). Therefore, the antibodies that bind to human IL-4R developed by the present invention can be used to prepare therapeutic drugs for patients with IL-4R overexpression diseases.

Antibody epitope analysis shows that the antibodies of the present invention specifically bind to the following amino acid residues on the extracellular domain of IL-4Rα: L39, F41, L42, L43, D72 and Y74.

Thus, a first object of the present invention is to provide an antibody or antigen-binding fragment thereof that binds to human IL-4R.

A second object of the present invention is to provide an isolated nucleotide encoding the antibody or antigen-binding fragment thereof that binds to human IL-4R.

A third object of the present invention is to provide an expression vector comprising the nucleotide.

A fourth object of the present invention is to provide a host cell comprising the expression vector.

A fifth object of the present invention is to provide a method for preparing the antibody or antigen-binding fragment thereof that binds to human IL-4R.

A sixth object of the present invention is to provide a pharmaceutical composition comprising the antibody or antigen-binding fragment thereof that binds to human IL-4R.

A seventh object of the present invention is to provide the use of the antibody or antigen-binding fragment thereof that binds to human IL-4R, or the pharmaceutical composition.

An eighth object of the present invention is to provide a method for improving the activity of the antibody or antigen-binding fragment thereof that binds to human IL-4R.

In order to achieve the above objects, the present invention adopts the following technical solutions:

The first aspect of the present invention provides an antibody or antigen-binding fragment thereof that binds to human IL-4R, comprising:

(a) heavy chain complementarity determining regions HCDR1, HCDR2, HCDR3, wherein the HCDR1 having the amino acid sequence as shown in SEQ ID NO: 6, the HCDR2 having the amino acid sequence as shown in SEQ ID NO: 7, and the HCDR3 having the amino acid sequence as shown in SEQ ID NO: 8, and (b) light chain complementarity determining regions LCDR1, LCDR2, LCDR3, wherein the LCDR1 having the amino acid sequence as shown in SEQ ID NO: 9, the LCDR2 having the amino acid sequence as shown in SEQ ID NO: 10, and the LCDR3 having the amino acid sequence as shown in SEQ ID NO: 11.

According to the present invention, the antibody is a monoclonal antibody or a polyclonal antibody. Preferably, the antibody is a monoclonal antibody.

According to the present invention, the antibody is a murine antibody, a chimeric antibody or a humanized antibody.

According to the present invention, the antibody is an IgG1-type antibody or an IgG4-type antibody.

According to the present invention, the antigen-binding fragment includes a Fab fragment, a F(ab')2 fragment, a Fv fragment, a single chain antibody (scFv) and a single domain antibody (sdAb), etc.

According to the present invention, the antibody or antigen-binding fragment thereof that binds to human IL-4R can block the interaction between IL-4 and IL-4R.

According to a preferred embodiment of the present invention, the antibody or antigen-binding fragment thereof that binds to human IL-4R comprises a heavy chain variable region having the amino acid sequence as shown in SEQ ID NO: 3, and a light chain variable region having the amino acid sequence as shown in SEQ ID NO: 5; and according to another preferred embodiment of the present invention, the antibody or antigen-binding fragment thereof that binds to human IL-4R comprises a heavy chain variable region having the amino acid sequence as shown in SEQ ID NO: 13, and a light chain variable region having the amino acid sequence as shown in SEQ ID NO: 15.

According to a preferred embodiment of the present invention, the antibody or antigen-binding fragment thereof that binds to human IL-4R comprises a heavy chain having the amino acid sequence as shown in SEQ ID NO: 16, and a light chain having the amino acid sequence as shown in SEQ ID NO: 18; and according to another preferred embodiment of the present invention, the antibody or antigen-binding fragment thereof that binds to human IL-4R comprises a heavy chain having the amino acid sequence as shown in SEQ ID NO: 17, and a light chain having the amino acid sequence as shown in SEQ ID NO: 18; and according to another preferred embodiment of the present invention, the antibody or antigen-binding fragment thereof that binds to human IL-4R comprises a heavy chain having the amino acid sequence as shown in SEQ ID NO: 19, and a light chain having the amino acid sequence as shown in SEQ ID NO: 18.

According to a preferred embodiment of the present invention, the antibody or antigen-binding fragment thereof that binds to human IL-4R comprises a Fc segment, and the Fc segment comprises the following mutation sites: S267E and L328F.

The second aspect of the present invention provides an isolated nucleotide, which encodes the antibody or antigen-binding fragment thereof that binds to human IL-4R as described in any one of the above.

According to a preferred embodiment of the present invention, the nucleotide has the nucleotide sequence encoding the heavy chain variable region as shown in SEQ ID NO: 2, and the nucleotide sequence encoding the light chain variable region as shown in SEQ ID NO: 4; in another preferred embodiment of the present invention, the nucleotide has the nucleotide sequence encoding the heavy chain variable region as shown in SEQ ID NO: 12, and the nucleotide sequence encoding the light chain variable region as shown in SEQ ID NO: 14.

The third aspect of the present invention provides an expression vector, which comprises the nucleotide as described in any one of the above.

The fourth aspect of the present invention provides a host cell, which comprises the expression vector as described above.

The fifth aspect of the present invention provides a method for preparing the antibody or antigen-binding fragment thereof that binds to human IL-4R described above, which comprises the following steps:

a) under expression conditions, cultivating the host cell as described above to express the antibody or antigen-binding fragment thereof that binds to human IL-4R, b) isolating and purifying the antibody or antigen-binding fragment thereof that binds to human IL-4R of step a).

The sixth aspect of the present invention provides a pharmaceutical composition, which comprises the antibody or antigen-binding fragment thereof that binds to human IL-4R as described in any one of the above, and a pharmaceutically acceptable carrier.

The seventh aspect of the present invention provides use of the antibody or antigen-binding fragment thereof that binds to human IL-4R as described in any one of the above, or the pharmaceutical composition as described above, for preparing a medicine for treating diseases related to IL-4R overexpression.

The present invention also provides a method for treating diseases related to IL-4R overexpression, which comprises administering to patients the antibody or antigen-binding fragment thereof that binds to human IL-4R of the present invention, or the pharmaceutical composition comprising the antibody or antigen-binding fragment thereof that binds to human IL-4R.

The present invention also provides an antibody or antigen-binding fragment thereof, or a pharmaceutical composition comprising the antibody or antigen-binding fragment thereof that binds to human IL-4R, for treating diseases related to IL-4R overexpression.

According to a preferred embodiment of the present invention, the diseases related to IL-4R overexpression include atopic dermatitis, asthma, allergic reactions, eosinophilic esophagitis, skin infections, nasal polyposis, etc.

The eighth object of the present invention is to provide a method for improving the activity of the antibody or antigen-binding fragment thereof that binds to human IL-4R as described in any one of the above; the antibody or antigen-binding fragment thereof that binds to human IL-4R comprises a Fc segment, wherein the Fc segment comprises the following mutation sites: S267E and L328F.

Advantageous Effect

The present in invention prepares a series of antibodies that bind to human IL-4R. They have identical variable regions and different constant regions. The variable regions can specifically bind to human IL-4R, and the constant regions affect the activity of the whole antibody through a unique mechanism. The series of antibodies mentioned above may be used for preparing medicines for treating IL-4R overexpression diseases (such as atopic dermatitis, asthma, etc.), and possesses good clinical application prospects.

DESCRIPTION OF THE DRAWINGS

FIG. 7-1 to FIG. 7-3 show the results of inhibitory effect of 4-2-Humanized-IgG1 and 4-2-Humanized-IgG4 on IL-4-induced TF-1 cell proliferation, detected by TF-1 cells.

FIG. 10-1 to FIG. 10-3 show the results of inhibitory effect of 4-2-Humanized-IgG1, 4-2-Humanized-IgG4, and 4-2-Humanized-IgG1-SELF on IL-4-induced CD23 expression on PBMC, detected by PBMC.

FIG. 11-1 to FIG. 11-2 show the results of inhibitory effect of 4-2-Humanized-IgG1, 4-2-Humanized-IgG4, and 4-2-Humanized-IgG1-SELF on IL-4-induced IgE secretion on PBMC, detected by PBMC.

DETAILED DESCRIPTION OF THE INVENTION

Figure 1:
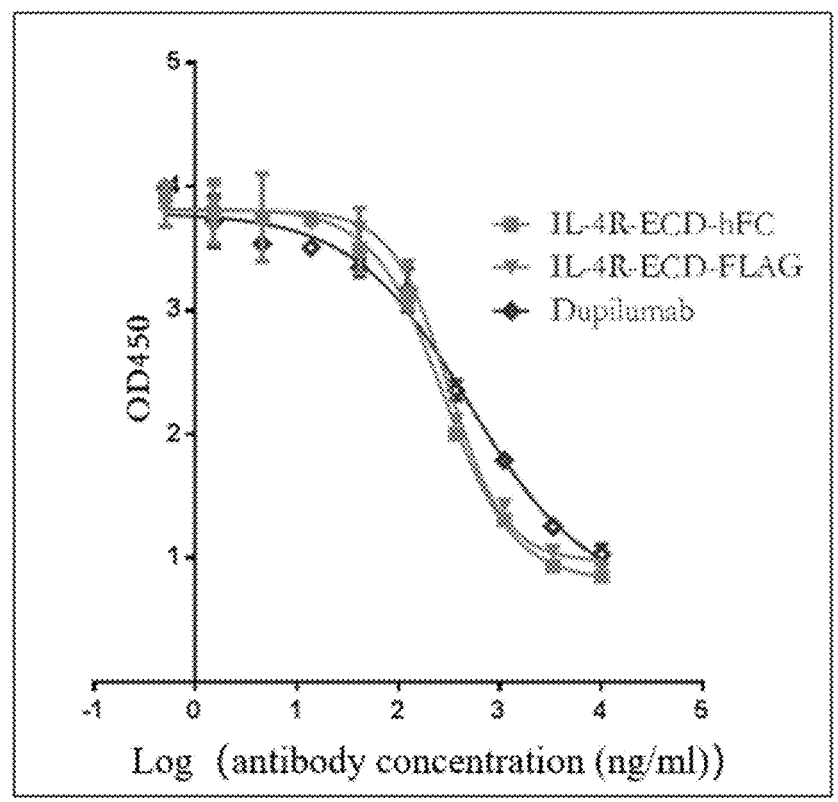
FIG. 1 shows the results of inhibitory effect of IL-4R-ECD-hFc and IL-4R-ECD-FLAG on IL-4-induced TF-1 cell proliferation, detected by TF-1 cells.

In the present invention, the terms "antibody (Ab)" and "immunoglobulin G (IgG)" are heterotetrameric glycoproteins of about 150,000 daltons with identical structural characteristics, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has a variable region (VH) at one end followed by constant regions. Each light chain has a variable region (VL) at one end and a constant region at its other end: the constant region of the light chain is aligned with the first constant region of the heavy chain, and the light chain variable region is aligned with the variable region of the heavy chain. The antibodies of the present invention include monoclonal antibodies, polyclonal antibodies, multispecific antibodies (such as bispecific antibodies) formed by at least two antibodies, antigen-binding fragments of antibodies, etc. The antibodies of the present invention comprise murine antibodies, chimeric antibodies, humanized antibodies, etc.

In the present invention, the term "monoclonal antibody (mAb)" refers to an antibody obtained from a population of substantially homogeneous antibodies, that is, the individual antibodies contained in the population are the same except for a few possible naturally occurring mutations. Monoclonal antibodies target a single antigen site with high specificity. Moreover, unlike conventional polyclonal antibody preparations (usually with different antibodies directed against different determinants), each monoclonal antibody is directed against a single determinant on the antigen. In addition to their specificity, the benefit of monoclonal antibodies is that they are synthesized by hybridoma culture and are not contaminated by other immunoglobulins. The modifier "monoclonal" indicates the characteristics of an antibody, which is obtained from a substantially uniform antibody population, and it should not be interpreted as requiring any special method to produce antibodies.

In the present invention, the term "murine antibody" refers to an antibody derived from rats or mice, preferably mice. The murine antibody of the present invention is obtained by immunizing mice with the extracellular domain of human IL-4R as an antigen and screening hybridoma cells. Preferably, the murine antibody of the present invention is antibody No. 4-2.

In the present invention, the term "chimeric antibody" refers to an antibody that comprises heavy and light chain variable region sequences from one species and constant region sequences from another species, such as an antibody having mouse heavy and light chain variable regions linked to human constant regions. Preferably, the chimeric antibody of the present invention is obtained by splicing the heavy chain variable region sequence and the light chain variable region sequence of the murine antibody No. 4-2 antibody with the human constant regions. More preferably, the heavy chain of the chimeric antibody of the present invention is obtained by splicing the heavy chain variable region sequence of the murine antibody No. 4-2 antibody with the constant region of human IgG1 or IgG4 (S228P), and the light chain is obtained by splicing the light chain variable region sequence of the murine antibody No. 4-2 antibody with human kappa chain. Most preferably, the chimeric antibody of the present invention is 4-2-Chimeric-IgG1.

In the present invention, the term "humanized antibody" means that the CDRs are derived from a non-human (preferably, mouse) antibody, while the remaining parts (including framework regions and constant regions) are derived from human antibody. In addition, framework region residues may be altered to preserve the binding affinity. Preferably, the humanized antibody of the present invention is obtained by recombining the CDR region of the murine antibody No. 4-2 antibody and the non-CDR region derived from a human antibody, and subjecting the embedded residues, the residues that directly interact with the CDR region, and the residues that have important influence on the conformation of VL and VH of antibody No. 4-2 to back mutation. More preferably, the humanized antibody of the present invention comprises 4-2-Humanized-IgG1 and 4-2-Humanized-IgG4.

In the present invention, the terms "binding", "specific binding", and "specifically binding" refer to the non-random binding reaction between two molecules, such as the reaction between an antibody and its targeted antigen. Generally, the antibody binds to the antigen with an equilibrium dissociation constant (KD) of less than about $10^{-5}$ M, for example, less than about $10^{-6}$ M, $10^{-7}$ M, $10^{-8}$ M, $10^{-9}$ M, or $10^{-10}$ M or less.

In the present invention, the term "KD" refers to the equilibrium dissociation constant of a specific antibody-antigen interaction, which is used to describe the binding affinity between the antibody and the antigen. The smaller the equilibrium dissociation constant is, the tighter the antibody-antigen binding is, and the higher the affinity between the antibody and the antigen is. Generally, the antibody binds to the antigen (such as IL-4R protein) with a KD of less than about $10^{-5}$ M, for example, less than about $10^{-6}$ M, $10^{-7}$ M, $10^{-8}$ M, $10^{-9}$ M or $10^{-10}$ M or less, for example, measured using surface plasmon resonance (SPR) technology with a BIACORE instrument.

In the present invention, the term "antigen-binding fragment" refers to a fragment of an antibody capable of specifically binding to an epitope of human IL-4R. Examples of the antigen-binding fragments of the present invention include Fab fragments, F(ab')2 fragments, Fv fragments, single chain antibodies (scFv), single domain antibodies (sdAb), etc. A Fab fragment is a fragment produced by digesting an antibody with papain. A F(ab')2 fragment is a fragment produced by digesting an antibody with pepsin. A Fv fragment is composed of dimers in which the variable region of the heavy chain and the variable region of the light chain of an antibody are closely and non-covalently linked. A single-chain antibody (scFv) is an antibody in which the variable region of the heavy chain and the variable region of the light chain of an antibody are linked by a short peptide (linker) of 15-20 amino acids. A single domain antibody (sdAb), also called nanobody or heavy chain antibody is composed of heavy chain only, and its antigen binding region is only a single domain linked to the Fc region through a hinge region.

In the present invention, the term "variable" refers to the fact that certain portions of the antibodies' variable regions differ in sequence, which is responsible for the binding specificity of various specific antibodies to their specific antigens. However, the variability is not evenly distributed in the variable regions of antibodies. It is concentrated in three segments called complementarity determining regions (CDRs) or hypervariable regions both in light chain and heavy chain variable regions. The relatively conserved portions of the variable regions are called the framework regions (FR). The variable regions of native heavy and light chains comprise respectively four FR regions, mostly in β-sheet configuration connected by three CDRs forming link loops and in some cases in partial β-sheet structure. The CDRs in each chain are held together closely through the FR regions and form the antigen binding site of antibodies with CDRs from another chain (see Kabat et al., NIH Publ.No. 91-3242, Volume I, Pages 647-669 (1991)). The constant regions are not involved directly in binding an antibody to an antigen, but they exhibit various effector functions, such as participation of antibody-dependent cell-mediated cytotoxicity (ADCC) and the like.

In the present invention, the term "Fc segment" means that papain can cleave an antibody into two identical Fab segments and one Fc segment. A Fc segment, namely fragment crystallizable (Fc), is composed of CH2 and CH3 domains of the antibody. A Fc segment has no antigen binding activity and is the site where the antibody interacts with effector molecules or cells.

In the present invention, the term "antibody that binds to human IL-4R" or "anti-human IL-4R antibody" refers to an antibody that specifically binds to human IL-4R. Preferably, the human IL-4R is the extracellular domain of human IL-4R. More preferably, the extracellular domain of human IL-4R has the amino acid sequence as shown in SEQ ID NO:1. Preferably, the antibody or antigen-binding fragment thereof that binds to human IL-4R of the present invention can block the interaction between IL-4 and IL-4R.

In the present invention, the term "expression vector" may be pTT5, pSECtag series, pCGS3 series, pCDNA series vectors, etc., as well as other vectors used in mammalian expression systems, etc. The expression vector comprises a fusion DNA sequence connected with appropriate transcription and translation regulatory sequences.

In the present invention, the term "host cell" refers to a cell suitable for expressing the expression vector described above. It may be a eukaryotic cell, such as mammalian or insect host cell culture system may be used to express the fusion protein of the present invention, CHO (Chinese hamster Ovary), HEK293, COS, BHK, etc. as well as derived cells of the above-mentioned cells are all suitable for the present invention.

In the present invention, the term "pharmaceutical composition" means that the antibody or antigen-binding fragment thereof that binds to human IL-4R of the present invention can be combined with pharmaceutically acceptable carriers to form pharmaceutical preparation compositions, so as to more stably exert a therapeutic effect. These preparations can ensure the conformational integrity of the amino acid core sequences of the antibody or antigen-binding fragment thereof that binds to human IL-4R disclosed in the present invention, and meanwhile, protect the multifunctional group of the protein from degradation (including but not limited to aggregation, deamination or oxidation).

In the present invention, the term "diseases related to IL-4R overexpression" means that the expression level of IL-4R in cells in an abnormal disease state is higher than the expression level of IL-4R in normal cells of the same tissue type. The diseases related to the overexpression of IL-4R of the present invention include but are not limited to: atopic dermatitis, asthma, allergic reactions, eosinophilic esophagitis, skin infections, nasal polyposis, etc.

The following examples and experimental examples further illustrate the present invention and should not be construed as limiting the present invention. The examples do not include a detailed description of traditional methods, such as those methods of constructing vectors and plasmids, methods of inserting genes encoding proteins into such vectors and plasmids or methods of introducing plasmids into host cells. Such methods are well known to those of ordinary skill in the art, and are described in many publications, including Sambrook, J., Fritsch, E. F. and Maniais, T. (1989) Molecular Cloning: A Laboratory Manual, 2nd edition, Cold spring Harbor Laboratory Press.

Example 1 Screening and Preparation of Murine Anti-Human IL-4R Monoclonal Antibody Example 1.1 Preparation of IL-4R Antigen and Positive Control Antibody Dupilumab The extracellular domain (IL-4R-ECD) sequence of the human IL-4Rα antigen having the amino acid sequence as shown in SEQ ID NO: 1. The amino acid sequence was subjected to codon optimization, whole gene synthesis, and then connected to a prokaryotic cloning vector. Recombinant PCR was used to add an hFc (IgG1) or FLAG tag to the end of the IL-4R-ECD coding region, the genes were recombined and then constructed into the pTT5 transient transfection vector (purchased from NRC biotechnology Research Institute). The above-mentioned vector was transfected into HEK293 cells (purchased from NRC biotechnology Research Institute) according to standard operating procedures, and cultured in Freestyle 293 Expression Medium (purchased from Gibco). After 5 days, the expressed IL-4R-ECD-hFc and IL-4R-ECD-FLAG antigens were purified from the cell culture supernatant. The above antigens were purified by protein A and anti-FLAG affinity chromatography columns, respectively.

The sequences of heavy chain and light chain of the positive control antibody Dupilumab were from WHO Drug Information (2013, 27(3): 284-285). The genes of heavy chain variable region and light chain variable region of the antibody were synthesized, and then recombined with human heavy chain IgG4 (S228P) and light chain Kappa constant region, respectively, and constructed into the pTT5 transient expression vector, respectively, expressed in HEK293E system, and purified by Protein A affinity chromatography.

After the above-mentioned proteins were purified, TF-1 cells were used to detect the ability of IL-4R-ECD-hFc, IL-4R-ECD-FLAG and Dupilumab to inhibit the proliferation of IL-4-induced TF-1 cells. TF-1 cells in logarithmic growth phase (purchased from ATCC) were washed twice with 37° C., pre-warmed complete RPM11640 medium (RPM11640 basal medium (purchased from Gibco) containing 10% fetal bovine serum), and centrifuged at 1000 rpm for 5 min; TF-1 cells were counted, suspended to a proper density in a complete medium containing RPM11640, inoculated into a 96-well plate at 10,000 cells/150 μl/well. IL-4 (purchased from R&D systems) was added in RPM11640 complete medium to a concentration of 80 ng/ml, then the medium containing IL-4 was used to dilute the human IL-4R antigens (IL-4R-ECD-hFc and IL-4R-ECD-FLAG) and the positive control antibody Dupilumab to a proper concentration, which was serially diluted into 9 gradients according to a proper ratio; and the diluted antigen and antibody were added into a 96-well cell culture plate at 50 μl/well. The periphery of the plate was filled with 200 μl/well of distilled water and incubated in a 37° C., 5% $CO_2$ incubator for 4 days. After 4 days, 20 μl of CCK-8 (purchased from Dojindo) solution was added to each well of the 96-well plate, which was incubated in a 37° C. incubator for another 8 hours. After mixing the cultural medium well by shaking, a microplate reader (SPECTRAMAX 190™ Molecular Devices) was used to read the OD450 values and GRAPHPAD PRISM-6™ was used to analyze data, prepare graphs, and calculate the IC50.

The results are shown in FIG. 1. IL-4R-ECD-hFc, IL-4R-ECD-FLAG and Dupilumab can effectively inhibit the IL-4-induced TF-1 cell proliferation, with an IC50 of 280.2 ng/ml, 315.1 ng/ml and 502.8 ng/ml, respectively.

Example 1.2 Immunization of Mice with Antigen

The TL-4R-ECD-hFc antigen prepared in Example 1.1 was diluted with normal saline to a proper concentration, mixed with an equal volume of Freund's complete adjuvant, fully phaco-emulsified, and then administrated to 4-5 weeks old Balb/c mice (purchased from Shanghai Lingchang Biotechnology Co., Ltd., animal production license number: SCXK (Shanghai) 2013-0018) by multipoint subcutaneous injection, with 50 μg antigen/100 μl per mouse. After three weeks, an equal amount of protein was mixed with an equal volume of Freund's incomplete adjuvant, fully phaco-emulsified, and then administrated to mice by multipoint subcutaneous immunization. Such immunization was repeated two weeks later. On the seventh day after the third immunization, one drop of blood was collected from each of all mice to separate serum, and the serum antibody titer was determined by ELISA. For nice with serum antibody titers >100,000, boosted immunization was performed one week after titer determination: injection of 10 μg antigen protein/100 μl normal saline/mouse by tail vein.

Wherein the method for determining serum titer by ELISA was as follows: IL-4R-ECD-hFc was diluted to 1000 ng/ml with sodium carbonate buffer (1.59 g $Na_2CO_3$ and 2.93 g $NaHCO_3$ dissolved in 1 L pure water), then added to an ELISA plate at 100 μl per well, incubated at room temperature for 4 hours. The plate was washed with phosphate buffer containing 0.05% Tween-20 (abbreviated as PBST: $KH_4PO_4$ 0.2 g, $Na_2HPO_4$-$12H_2O$ 2.9 g, NaCl 8.0 g, KCl 0.2 g, Tween-20 0.5 ml, adding pure water to 1000 ml); and blocked by adding PBST containing 1% bovine serum albumin (BSA) to each well. The plate was washed with PBST, added with gradiently-diluted mouse serum, and incubated for a proper period of time. The plate was washed with PBST, added with a properly diluted HRP-labeled goat anti-mouse secondary antibody, and incubated for a proper period of time. After the plate was washed, the chromogenic solution (chromogenic substrate solution A: sodium acetate trihydrate 13.6 g, citric acid monohydrate 1.6 g, 30% hydrogen peroxide 0.3 ml, pure water 500 ml; chromogenic substrate solution B: ethylenediaminetetraacetic acid disodium 0.2 g, citric acid monohydrate 0.95 g, glycerol 50 ml, TMB: 0.15 g dissolved in 3 ml DMSO, pure water 500 ml; A and B mixed well in equal volumes before use) was used for color development, and a stop solution (2 M sulfuric acid solution) was used to stop the color reaction. A microplate reader was used to read the OD450, and GRAPHPAD PRISM-6™ was used to analyze data, prepare graphs, and calculate serum titers.

Example 1.3 Preparation and Screening of Hybridornas

Spleen cells of the mice were taken for fusion three days after the boosted immunization. Myeloma sp2/0 cells in good-growth condition (derived from the Cell Bank of the Typical Cell Culture Collection Committee of the Chinese Academy of Sciences) were cultured in a 37° C., 5% $CO_2$ incubator and changed medium the day before fusion. The fusion and screening processes were as follows: the spleens of the mice were taken, ground, washed and counted. The spleen cells and sp2/0 cells were mixed in a ratio of 2:1, centrifuged at 1500 rpm for 7 minutes and discarded the supernatant. Under the condition of centrifuging at 1000 rpm for 5 min, 20 ml of cell fusion buffer (purchased from BTX) was added to wash the cells three times. The cell pellets were suspended in the cell fusion buffer at a density of $1 \times 10^7$ cells/ml. 2 ml of the cell suspension was added to the fusion pool, placed on electrofusion machine ECM2001, and subjected to electrofusion within 30 seconds according to certain conditions (AC60V, 30S; DC1700V, 40US, 3X; POST AC60V, 3S). After electrofusion, the fused cells were gently transferred to a 37° C., pre-warmed RPMI1640 medium containing 10% serum (purchased from Gibco), and standed at room temperature for another 60 min. 100 W/well, the cells were inoculated into a 96-well plate at $10^4$ cells/well. The next day, each well was supplemented with 100 μl of RPMI1640 medium containing 2×HAT (purchased from Gibco) and 10% serum. On the fourth day after fusion, half of the medium was renewed with fresh RPMI1640 medium containing 1×HAT. On the seventh day after fusion, most of the medium was renewed with fresh RPM11640 medium containing 1×HAT. On the ninth day after fusion, samples were taken for ELISA test. Positive hybridoma clones were selected and expanded in a 24-well plate and subcloned by limiting dilution. Hybridoma strains stably expressing the target antibody were obtained by the above-mentioned method, and these cell clones were expanded and frozen. The above-mentioned hybridoma strains were cultured in serum-free medium HybriGRO SF (purchased from Corning) for 7 days, and then murine anti-human IL-4R monoclonal antibody was purified from the culture supernatant using Protein A/G affinity chromatography column.

See Example 1.2 for the ELISA test method, except that IL-4R-ECD-hFc was replaced with IL-4R-ECD-FLAC.

Example 1.4 ELISA Test

In this example, ELISA method was used to test the relative affinity of the purified murine anti-human IL-4R monoclonal antibodies for IL-4R antigen.

See Example 1.2 for the experimental method, except that IL-4R-ECD-hFc was diluted to 100 ng/ml with sodium carbonate buffer. Wherein, the negative control used was a murine antibody that does not bind to human IL-4R.

Figure 2:
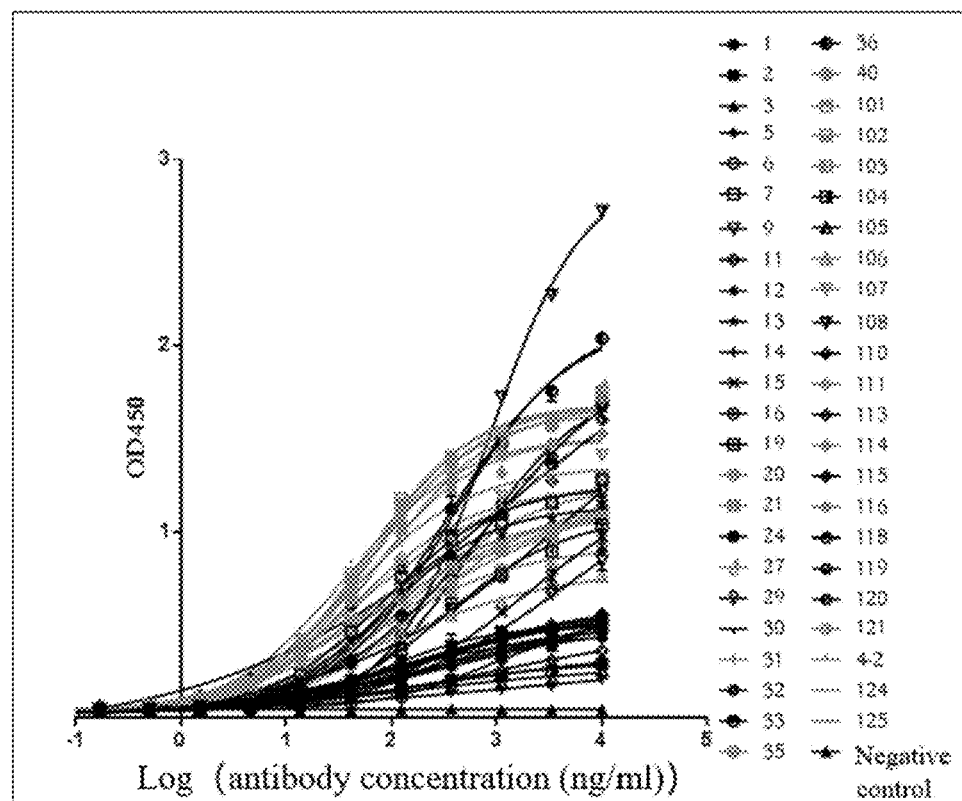
FIG. 2 shows the results of relative affinity of purified murine anti-human IL-4R monoclonal antibody to IL-4R antigen, detected by ELISA.

The results are shown in FIG. 2. According to the EC50 data, the antibodies with higher relative affinity were selected and advanced to the next screening session.

Example 1.5 Inhibitory Effects on IL-4-Induced TF-1 Cell Proliferation

In this example, TF-1 cells were used to test inhibitory effects of the purified murine anti-human IL-4R monoclonal antibodies on IL-4-induced TF-1 cell proliferation.

See Example 1.1 for the experimental method.

Figure 3:
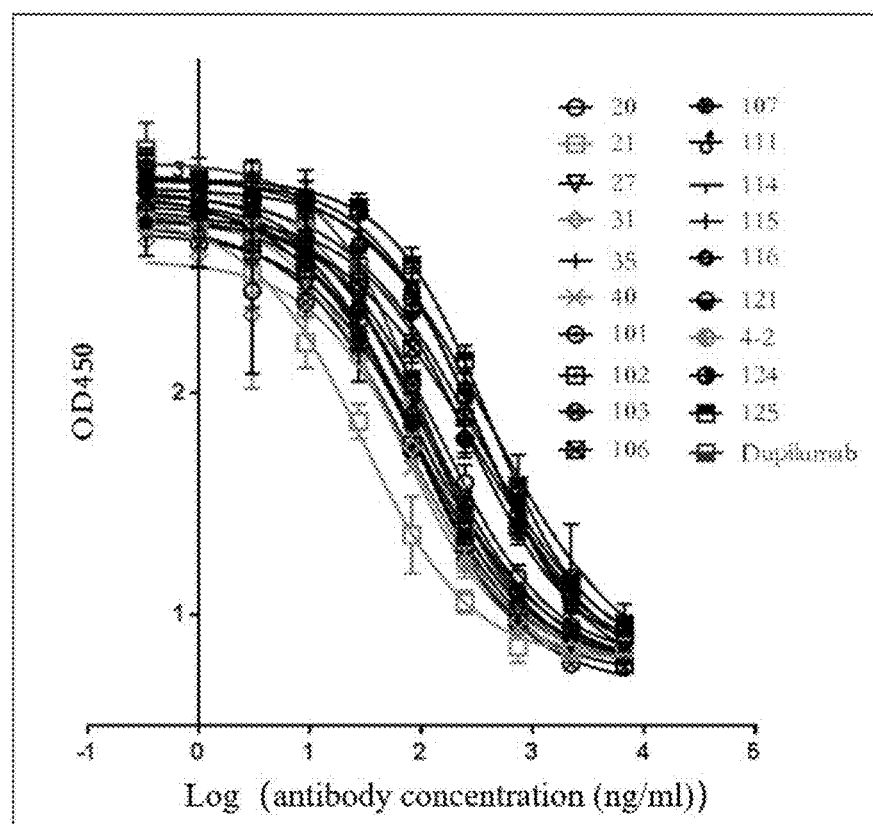
FIG. 3 shows the results of inhibitory effect of purified murine anti-human IL-4R monoclonal antibody on IL-4-induced TF-1 cell proliferation, detected using TF-1 cells.

The results are shown in FIG. 3. According to the IC50 data, the monoclonal antibodies with strong inhibitory effect were selected and advanced to the next experiment.

Example 2 Humanization of Murine Anti-Human IL-4R Monoclonal Antibody

Example 2.1 Determination of Variable Region Sequences of Murine Anti-Human IL-4R Monoclonal Antibody According to the screening results of ELISA and functional experiment at the cellular level in Examples 1.4 and 1.5, clones No. 21, 31, 40 and 4-2 were finally picked as the lead antibodies. Total RNA was extracted from hybridoma monoclonal cell strains corresponding to the four monoclonal antibodies using Trizol (purchased from Life technologies), and mRNA was reverse transcribed into cDNA using a reverse transcription kit (purchased from Takara). By the combined primers reported in the literature ("Antibody Engineering", Volume 1, Edited by Roland Kontermann and Stefan Dübel; the sequences of the combined primers are from page 323), the genes of light chain variable region and heavy chain variable region of the murine anti-human IL-4R monoclonal antibodies were amplified by PCR, then the PCR products were cloned into pMD18-T vector, and the variable region genes were sequenced and analyzed. After comparative analysis of the variable region sequences of each clone, it was found that the sequences of antibody No. 4-2 were more suitable for humanization. So clone No. 4-2 was selected as the final candidate antibody. Its sequence information is as follows: the heavy chain variable region gene sequence is 360 bp in length, encoding 120 amino acid residues, the nucleotide sequence of which is shown in SEQ ID NO: 2 and the amino acid sequence is shown in SEQ ID NO: 3. The light chain variable region gene sequence is 318 bp in length, encoding 106 amino acid residues, the nucleotide sequence of which is shown in SEQ ID NO: 4 and the amino acid sequence is shown in SEQ ID NO: 5.

Example 2.2 Humanization of Murine Anti-Human IL-4R Monoclonal Antibody

The amino acid sequences of the light chain variable region and the heavy chain variable region mentioned above were analyzed, and three complementarity-determining regions (CDRs) and four frame regions (FRs) of the antibody No. 4-2 were identified according to the Kabat rule. Wherein, the amino acid sequences of the heavy chain complementarity determining regions are: HCDR1: DDYIN (SEQ ID NO: 6), HCDR2: WIFPGNGNSYYNEKFKD (SEQ ID NO: 7) and HCDR3: GLVRYRALFDY (SEQ ID NO: 8), the amino acid sequences of the light chain complementarity determining regions are: LCDR1: RASSSINYMH (SEQ ID NO: 9), LCDR2: AASNLAS (SEQ ID NO: 10) and LCDR3: QQWSSYPIT (SEQ ID NO: 11).

By homology comparison with human IgG germline sequence (Germline) at NCBI IgBlast, IGHV1-3*01 was selected as the heavy chain CDR graft template. The heavy chain CDRs of murine antibody No. 4-2 were transplanted into the framework region of IGHV1-3*01 to construct a heavy chain CDR-grafted antibody. Similarly, by homology comparison with human IgG germline sequence, IGKV1-16*01 was selected as the light chain CDR graft template, and the light chain CDRs of the murine antibody No. 4-2 were transplanted into the framework region of IGKV1-16*01 to construct a light chain CDR-grafted antibody which was defined as 4-2-Grafted. Meanwhile, on this basis, some amino acid sites in the framewvork regions were subjected to back mutation. The back mutation refers to mutation of certain amino acids in the human framework region to the ones at the same position in the murine framework region. When back mutation was performed, the amino acid sequences were encoded by Kabat numbering system and the positions were indicated by Kabat numbering. Preferably, for the heavy chain variable region sequence, M at position 48 by Kabat numbering was back mutated to murine V, V at position 67 was back mutated to A, I at position 69 was back mutated to L, R at position 71 was back mutated to V, T at position 73 was back mutated to K, and Y at position 91 was back mutated to F. For the light chain variable region sequence, F at position 36 by Kabat numbering was back mutated to Y, S at position 46 was back mutated to P, and L at position 47 was back mutated to W. The above variable region gene sequences were codon-optimized and synthesized according to the codon usage preference of *Cricetulus griseus* by Suzhou Jinweizhi Company. The synthesized humanized heavy chain variable region sequence was linked to human IgG1 and IgG4 (S228P) constant regions, respectively, and the resulting genes were named 4-2-Humanized-IgG1-HC and 4-2-Humanized-IgG4-HC, respectively. The humanized light chain variable region was linked to human Kappa chain constant region, and the resulting gene was named 4-2-Humanized-LC. In addition, the murine heavy chain variable region sequence was linked to human IgG1 and IgG4 (S228P) constant regions, respectively, and the resulting genes were named 4-2-Chimeric-IgG1-HC and 4-2-Chimeric-IgG4-HC, respectively. The munne light chain variable region was linked to human Kappa chain constant region, and the resulting gene was named 4-2-Chimeric-LC.

Finally, the humanized heavy chain variable region gene sequence of antibody No. 4-2 is 360 bp in full length, encoding 120 amino acid residues, the nucleotide sequence of which is shown in SEQ ID NO: 12 and the amino acid sequence is shown in SEQ ID NO: 13; the humanized light chain variable region gene sequence is 318 bp in length, encoding 106 amino acid residues, the nucleotide sequence of which is shown in SEQ ID NO: 14, and the amino acid sequence is shown in SEQ ID NO: 15. After the humanized heavy chain variable region was linked to human IgG1 constant region, a 4-2-Humanized-TgG1-HC heavy chain having 447 amino acids was finally obtained (sequence shown in SEQ ID NO: 16); after the humanized heavy chain variable region was linked to human IgG4 (S228P) constant region, a 4-2-Humanized-IgG4-IC heavy chain (sequence shown in SEQ ID NO: 17) having 447 amino acids was finally obtained; after the light chain variable region was linked to human Kappa constant region, a 4-2-Humanized-LC light chain having 213 amino acids was obtained (sequence shown in SEQ ID NO: 18).

The light and heavy chain genes of the above antibodies were constructed into the pTT5 expression vector, and the expression vectors of above light and heavy chains were combined and then transiently transfected using HEK293E system to express the antibodies. HEK293 cells were cultured in Free Style 293 Expression Medium. Plasmid was transferred into the cells by PEI transfection method and the cell supernatant was collected after 5 days. Purified antibodies were obtained by protein A affinity chromatography. The antibodies obtained from the combined expression of 4-2-Humanized-IgG1-HC and 4-2-Humanized-IgG4-1C with 4-2-Humanized-LC were defined as 4-2-Humanized-IgG1 and 4-2-Humanized-IgG4, respectively. In addition, the antibody obtained from combined expression of 4-2-Chimeric-IgG1-HC and 4-2-Chimeric-LC was defined as 4-2-Chimeric-ILG1.

Example 3 Test of the Functional Activities of Chimeric Antibody 4-2-Chimeric-IgG1 and Humanized Antibody 4-2-Humanized-IgG1

Example 3.1 ELISA Test

In this example, an ELISA method was used to detect the relative affinities of 4-2-Chimeric-IgG1 and 4-2-Humanized-IgG1 for IL-4R antigen.

See Example 1.2 for the experimental method, except that IL-4R-ECD-hFc was replaced with IL-4R-ECD-FLAG (IL-4R-ECD-FLAG was diluted to 100 ng/ml with sodium carbonate buffer), and HRP-labeled goat anti-mouse secondary antibody was replaced with HRP-labeled goat anti-human secondary antibody. Wherein, the negative control antibody used was a humanized antibody that does not bind to human IL-4R.

Figure 4:
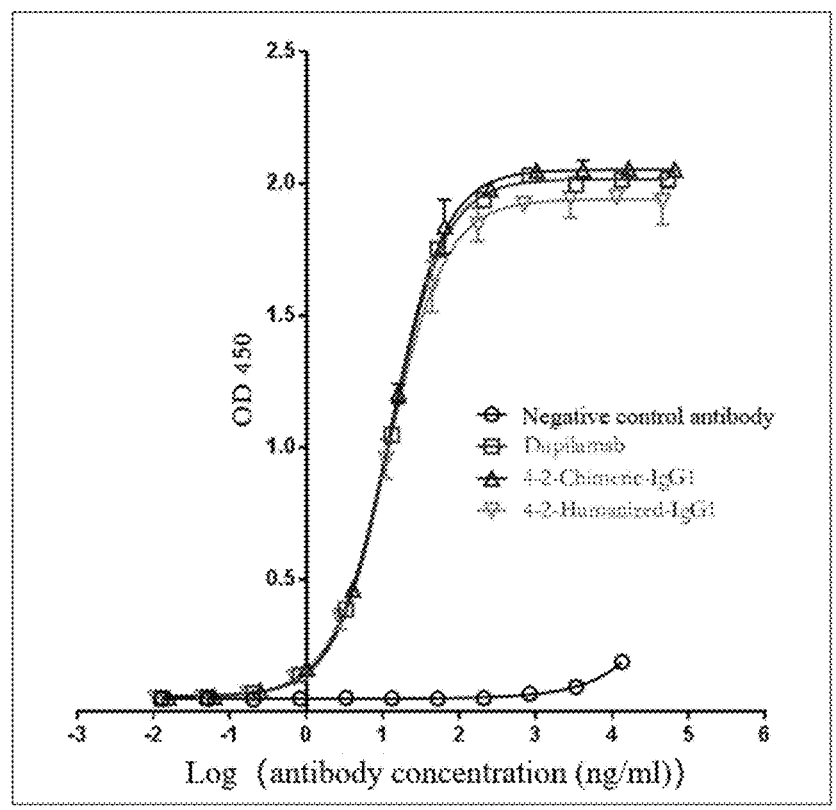
FIG. 4 shows the results of relative affinity of 4-2-Chimeric-IgG1 and 4-2-Humanized-IgG1 for IL-4R antigen, detected by ELISA.

As shown in FIG. 4, 4-2-Humanized-IgG1, 4-2-Chimeric-IgG1 and Dupilumab can effectively bind to the antigen IL-4R-ECD-FLAG, with an EC50 of 12.39 ng/ml 11.81 ng/ml and 12.52 ng/ml, respectively.

Example 3.2 Inhibitory Effects on IL-4-Induced TF-1 Cell Proliferation

In this example, TF-1 cells were used to detect inhibitory effects of 4-2-Chimeric-IgG1 and 4-2-Humanized-IgG1 on IL-4-induced TF-1 cell proliferation.

See Example 1.1 for the experimental method. Wherein, the negative control used did not contain IL-4 but contained a control antibody that does not bind to human IL-4R; the positive control contained IL-4 and a control antibody that does not bind to human IL-4R.

Figure 5:
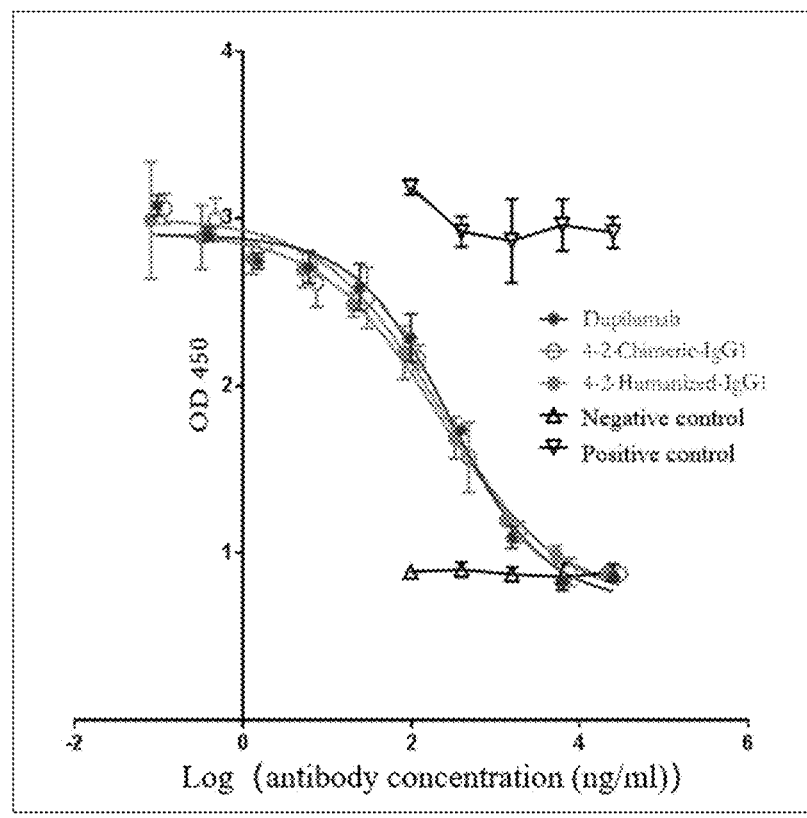
FIG. 5 shows the results of inhibitory effect of 4-2-Chimeric-IgG1 and 4-2-Humanized-IgG1 on IL-4-induced TF-1 cell proliferation, detected by TF-1 cells.

As shown in FIG. 5, Dupilumab, 4-2-Chimeric-IgG1 and 4-2-Humanized-IgG1 can effectively inhibit the IL-4-induced TF-1 cell proliferation, with an IC50 of 289.4 ng/ml, 225.2 ng/ml and 207.4 ng/mi, respectively.

Example 3.3 Inhibitory Effects on IL-13-Induced TF-1 Cell Proliferation

In this example, TF-1 cells were used to detect inhibitory effects of 4-2-Chimeric-IgG1 and 4-2-Humanized-IgG1 on IL-13-induced TF-1 cell proliferation.

See Example 1.1 for the experimental method, except that IL-4 was replaced with IL-13, wherein, the negative control used did not contain IL-13 but contained a control antibody that does not bind to human IL-4R; the positive control contained IL-13 and a control antibody that does not bind to human IL-4R antibody.

Figure 6:
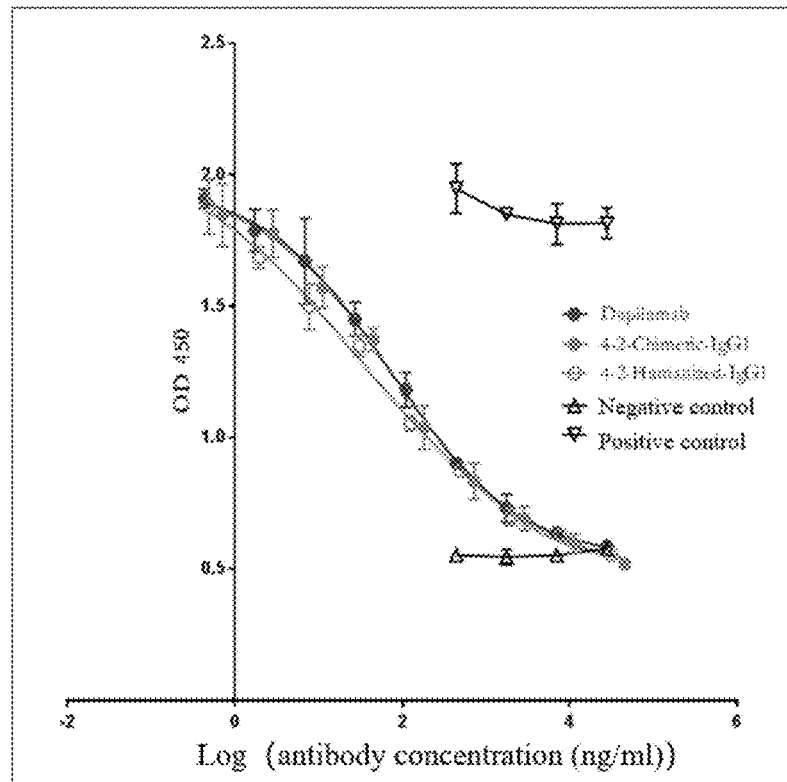
FIG. 6 shows the results of inhibitory effect of 4-2-Chimeric-IgG1 and 4-2-Humanized-IgG1 on IL-13-induced TF-1 cell proliferation, detected by TF-1 cells.

As shown in FIG. 6, Dupilumab, 4-2-Chimeric-IgG1 and 4-2-Humanized-IgG1 can effectively inhibit IL-13-induced TF-1 cell proliferation, with an IC50 of 73.8 ng/ml, 81.6 ng/ml and 34.3 ng/ml, respectively.

Example 4 Detection of Functional Activities of Humanized Antibodies 4-2-Humanized-IgG1 and 4-2-Humanized-IgG4

Example 4.1 Inhibitory Effects on IL-4-Induced TF-1 Cell Proliferation

In this example, TF-1 cells were used to detect the inhibitory effects of humanized antibodies 4-2-Humanized-IgG1 and $4^{-2}$-Humanized-IgG4 on IL-4-induced TF-1 cell proliferation.

See Example 1.1 for the experimental method. Wherein the negative control used did not contain IL-4 but contained a control antibody that does not bind to human IL-4R; the positive control contained IL-4 and a control antibody that does not bind to human IL-4R.

Figures 1, 7:
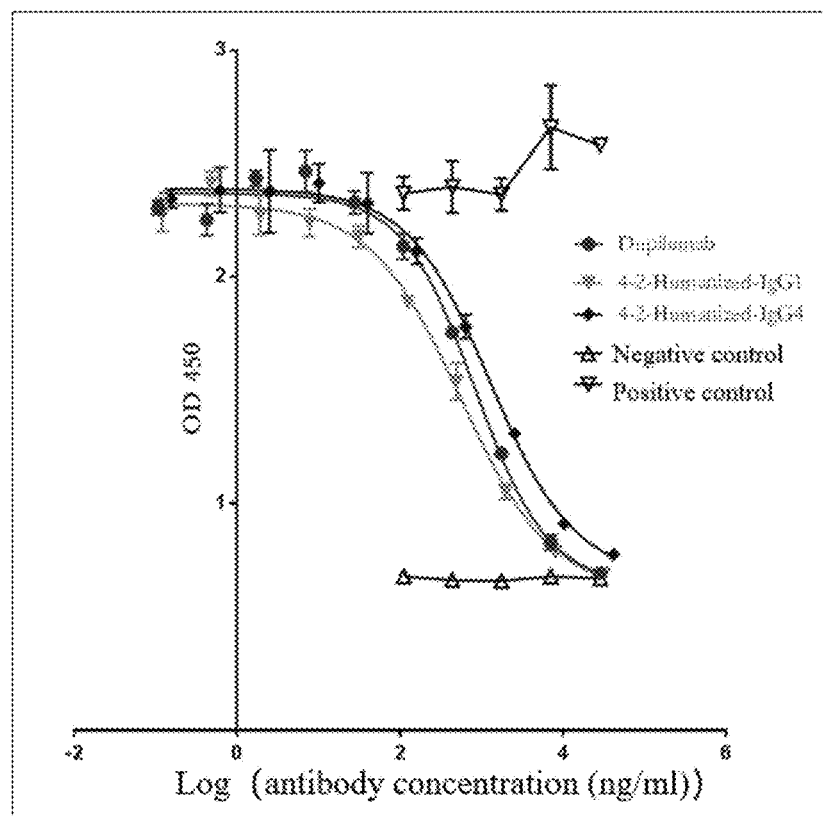
Figures 2, 7:
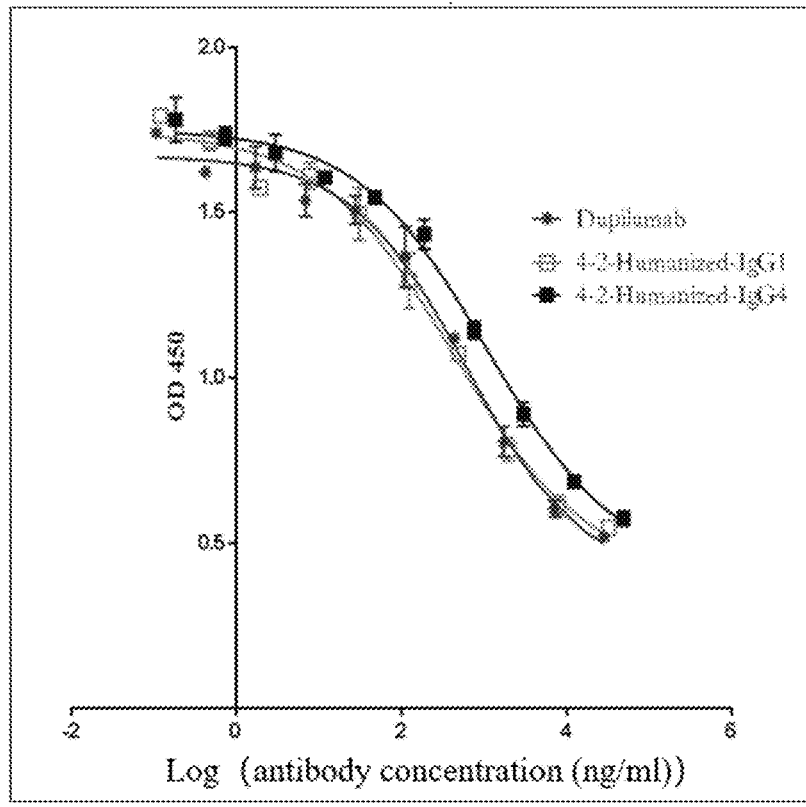
Figures 3, 7:
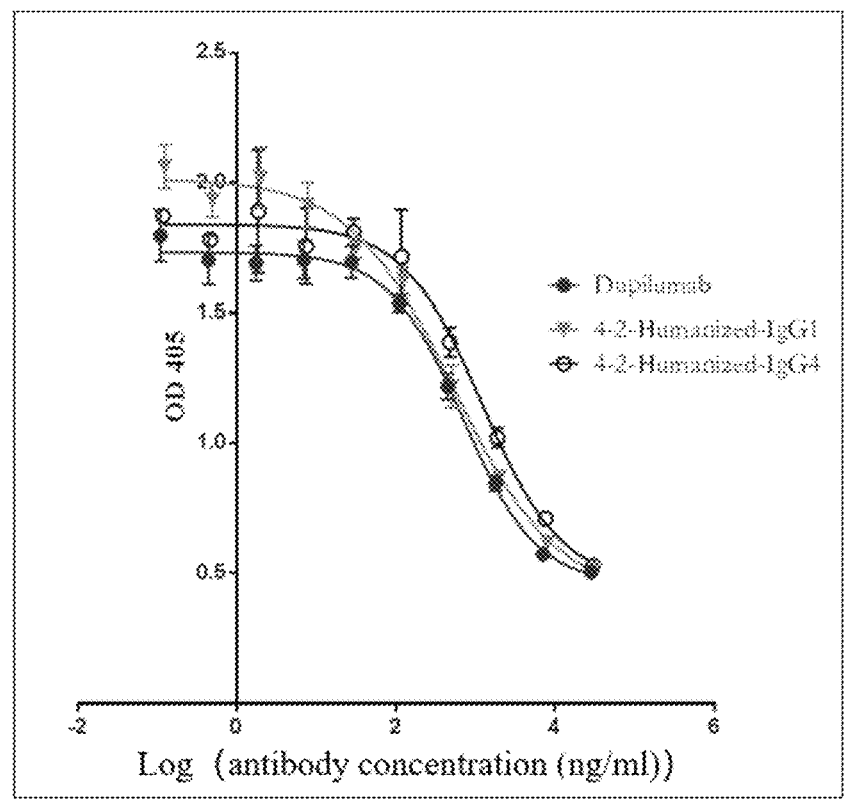

The results of the first experiment are shown in FIG. 7-1. The IC50s of Dupilumab, 4-2-Humanized-IgG1 and 4-2-Humanized-IgG4 for the inhibition of IL-4-induced TF-1 cell proliferation were 841.6 ng/ml, 560.6 ng/ml and 1291 ng/ml, respectively. The results of the second repeated experiment are shown in FIG. 7-2. The IC50s of Dupilumab. 4-2-Humanized-IgG1 and 4-2-Humanized-IgG4 for the inhibition of IL-4-induced TF-1 cell proliferation were 616.1 ng/ml, 426.9 ng/ml and 1113 ng/ml, respectively. The results of the third repeated experiment are shown in FIG. 7-3. The IC50s of Dupilumab, 4-2-Humanized-IgG1 and 4-2-Humanized-IgG4 for the inhibition of IL-4-induced TF-1 cell proliferation were 687.1 ng/ml, 520.4 ng/ml and 1145 ng/ml, respectively. The functional activity intensity of all the three repeated independent experiments was ranked as follows: 4-2-Humanized-IgG1>Dupilumab>4-2-Humanized-IgG4. Statistical analysis of the results of the three experiments show that there is a significant difference between 4-2-Humanized-IgG1 and Dupilumab (P=0.026<0.05; the statistical method was T-test, P<0.05 was considered as statistically significant), indicating that the functional activity of 4-2-Humanized-IgG1 is stronger than Dupilumab.

Example 4.2 Biacore Detection

In this example, the affinities of 4-2-Humanized-IgG1 and 4-2-Humanized-IgG4 for IL-4R were detected by Biacore T200 (GE healthcare).

The capture molecule Protein A/G was covalently coupled to the chip surface using the activation reagent EDC/NHS and the blocking reagent Ethanolamine in the amino coupling kit (purchased from GE healthcare); on the Biacore T200, IL-4R antibody was captured using the CM5 chip coupled with ProteinA/G, and then IL-4R-ECD-FLAG was injected, to obtain a binding-dissociation curve. Next cycle was repeated after eluting the chip with 6 M guanidine hydrochloride regeneration buffer. The data was analyzed using Biacore T200 Evaluation Software. The results are shown in Table 1.

TABLE 1

Detection of affinities of 4-2-Humanized-IgG1/4 for human IL-4R

| Sample Name | Kon (1/Ms) | Koff (1/s) | KD (M) |
|---|---|---|---|
| Dupilumab | 5.88E+04 | 3.95E−05 | 6.71E−10 |
| 4-2-Humanized-IgG1 | 1.86E+05 | 1.33E−04 | 7.17E−10 |
| 4-2-Humanized-IgG4 | 1.88E+05 | 1.30E−04 | 6.92E−10 |

The experimental results showed that the affinities of 4-2-Humanized-IgG1 and 4-2-Humanized-IgG4 for IL-4R were equivalent to that of Dupilumab, being 7.17E-10, 6.92E-10 and 6.71E-10, respectively. Both 4-2-Humanized-IgG1 and 4-2-Humanized-IgG4 can bind IL-4R faster than Dupilumab.

Example 5 Construction of SELF Mutant of Anti-Human IL-4R Humanized Antibody The experimental results in Example 4.1 showed that, compared with 4-2-Humanized-IgG1, 4-2-Humanized-IgG4 was slightly weaker in functional activity on inhibition of IL-4-induced TF-1 cell proliferation while the Biacore affinity detection results in Example 4.2 showed that 4-2-Humanized-IgG1 and 4-2-Humanized-IgG4 had substantially the same affinity for IL-4R, indicating that such difference was not caused by affinity change. The above results suggest that the difference in activity between 4-2-Humanized-IgG1 and 4-2-Humanized-IgG4 in Example 4.1 may be caused by difference between Fc segments of the antibodies.

The patent US20090136485A1 disclosed by Xencor, Inc. reported that introduction of S267E+L328F mutation into constant region of Fc segment of antibodies (simultaneous mutation of S at position 267 to E and L at position 328 to F) can enhance the interaction between Fc segment and CD32 molecule (a Fc receptor molecule) by about 400 times (Chu S Y, Vostiar I, Karki S, et al. Inhibition of B cell receptor-mediated activation of primary human B cells by coengagement of CD19 and Fc.gamma.RIIb with Fc-engineered antibodies. J. Molecular immunology, 2008, 45(15): 3926-3933). The present invention introduced the S267E+L328F mutation into Fc coding region of 4-2-Humanized-IgG1-HC, and the heavy chain gene of the mutant antibody was named 4-2-Humanized-IgG1-HC-SELF. Said heavy chain gene was combined with 4-2-Humanized-LC, and then expressed in HEK293E cells, according to the specific expression and purification methods described in Examples 1.1 and 2.2. The final obtained mutant antibody was defined as 4-2-Humanized-IgG1-SELF. The amino acid position of the antibody sequence in this example adopted Eu coding method. Wherein, the heavy chain of 4-2-Humanized-IgG1-SELF antibody has the amino acid sequence as shown in SEQ ID NO: 19.

Example 6 Detection of Functional Activities of SELF Mutant and Non-SELF Mutant of Anti-Human IL-4R Humanized Antibody

Example 6.1 Blocking Activities on the Interaction of IL-4 and IL-4R

In this example, ELISA was used to detect the blocking activities of 4-2-Humanized-IgG1, 4-2-Humanized-IgG4 and 4-2-Humanized-IgG1-SELF on the interaction of IL-4 and IL-4R.

The human IL-4 sequence had the amino acid sequence as shown in SEQ ID NO: 20. The amino acid sequence was subjected to codon optimization, whole gene synthesis, and then linked to a prokaryotic cloning vector. Recombinant PCR was used to add an hFc (IgG1) tag to the end of the human IL-4 coding region. After recombination, the genes were constructed into the pTT5 transient transfection vector. The above vector was transfected into HEK293 cells according to standard operating procedures, and cultured in Freestyle 293 Expression Medium. After 5 days, the expressed IL-4-hFc was purified from the cell culture supernatant. The above antigen was purified by protein A affinity chromatography. The purified IL-4-hFc was used as the ligand for blocking detection. IL-4R-ECD-hFc, which had been subjected to dialysis and concentration determination, was biotinylated with Biotin N-hydroxysuccinimide ester (Sigma/Cat. No. H1759-100 MG).

IL-4-hFc was diluted to 2000 ng/ml with sodium carbonate buffer, then added to an ELISA plate at 100 μl per well, and incubated at room temperature for 4 hours. The plate was washed with phosphate buffer containing 0.05% Tween-20 (PBST) and blocked by adding PBST containing 1% bovine serum albumin to each well. Then the plate was washed with PBST. The Biotinated IL-4R-ECD-hFc was diluted in PBST to a final concentration of 100 ng/ml, and the solution obtained was used to properly dilute the antibody to be tested. The diluted antibody was then subjected to gradient dilution in a 96-well plate, and then transferred to the above ELISA plate coated with IL-4-hFc and incubated at room temperature for 1 hour. The plate was washed with PBST. Streptavidin-HRP which was diluted with PBST containing 1% BSA at a dilution ratio of 1:1000 was added at 100.mu·l/well and incubated at 37° C. for 30 min. Chromogenic solution (TMB substrate solution) was added at 100 μl/well, and incubated at room temperature for 1.about 0.5 min; then 50 μl/well of the stop solution was added to stop the color reaction. OD450 values were read with a microplate reader and GRAPHPAD PRISM-6™ was used to analyze data, prepare graphs, and calculate IC50. Wherein, the negative control antibody used was a humanized antibody that does not bind to human IL-4R.

Figure 8:
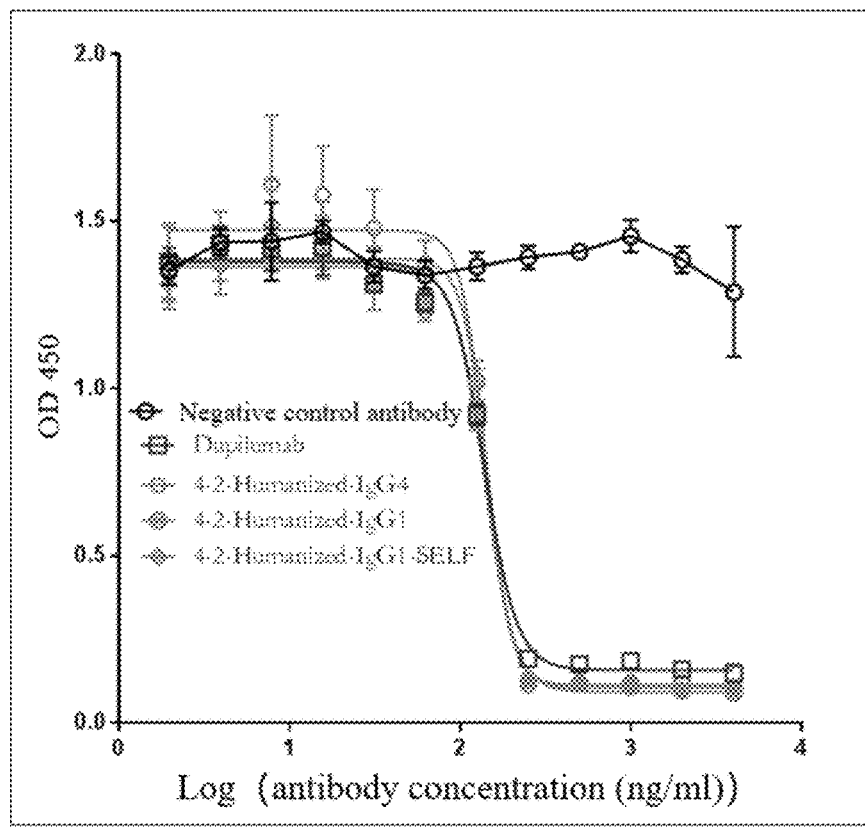
FIG. 8 shows the results of blocking activity of 4-2-Humanized-IgG1, 4-2-Humanized-IgG4 and 4-2-Humanized-IgG1-SELF on the interaction of IL-4 and IL-4R, detected by ELISA.

As shown in FIG. 8, Dupilumab, 4-2-Humanized-IgG4, 4$^{-2}$-Humanized-IgG1 and 4-2-Humanized-IgG1-SELF can effectively block the interaction between IL-4 and IL-4R, with an IC50 of 137.9 ng/ml, 140.3 ng/ml, 138.3 ng/ml and 144.1 ng/ml, respectively. The above results suggest that Dupilumab, 4-2-Humanized-IgG4, 4-2-Humanized-IgG1 and 4-2-Humanized-IgG1-SELF have substantially identical abilities to block the interaction between IL-4 and IL-4R, without significant difference.

Example 6.2 Inhibitory Effects on IL-4-Induced TF-1 Cell Proliferation

In this example, TF-1 cells were used to detect the inhibitory effects of 4-2-Humanized-IgG1, 4-2-Humanized-IgG4, and 4-2-Humanized-IgG1-SELF on IL-4-induced TF-1 cell proliferation.

See Example 1.1 for the experimental method. Wherein the negative control used did not contain IL-4 but contained a control antibody that does not bind to human IL-4R; the positive control contained IL-4 and a control antibody that does not bind to human IL-4R.

Figure 9:
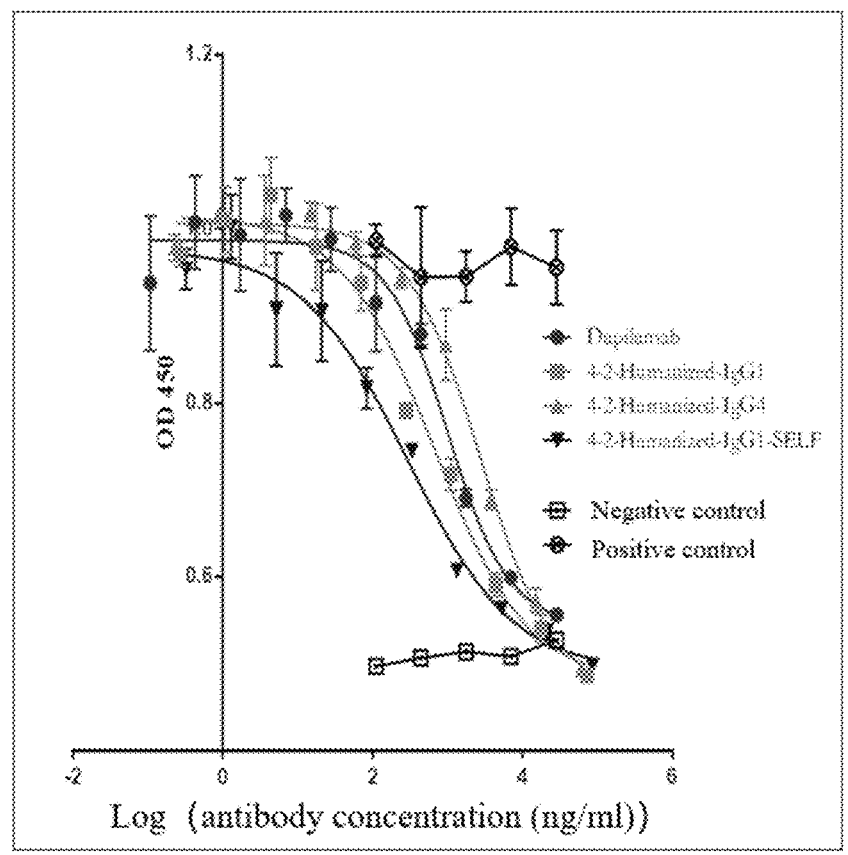
FIG. 9 shows the results of inhibitory effect of 4-2-Humanized-IgG1, 4-2-Humanized-IgG4, and 4-2-Humanized-IgG1-SELF on IL-4-induced TF-1 cell proliferation, detected by TF-1 cells.

As shown in FIG. 9, the IC50s of inhibitory effect of Dupilumab, 4-2-Humanized-IgG1, 4-2-Humanized-IgG4 and 4-2-Humanized-IgG1-SELF on IL-4-induced TF-1 cell proliferation were 1008 ng/ml, 667.7 ng/ml, 2782 ng/ml and 291.9 ng/ml, respectively. The functional activity intensity was ranked as follows: 4-2-Humanized-IgG1-SELF>4-2-Humanized-IgG1>Dupilumab>4-2-Humanized-IgG4.

Example 6.3 Inhibitory Effects on IL-4-Induced CD23 Expression by PBMC

IL-4 can induce human peripheral blood mononuclear cells (PBMC) to express CD23 molecules. CD23 molecule is a low-affinity IgE receptor associated with allergic reactions. In this example, PBMCs were used to detect the inhibitory effects of 4-2-Humanized-IgG1, 4-2-Humanized-IgG4, and 4-2-Humanized-IgG1-SELF on IL-4-induced CD23 expression by PBMC.

PBMCs were separated from human whole blood using Histopaque, and the cells were counted and then inoculated into a round-bottom 96-well cell culture plate using RMPI-1640 complete medium (containing 10% fetal bovine serum) at 2E5 cells/150 µl per well. IL-4 was diluted to 80 ng/ml with RMPI-1640, and the obtained medium was used to dilute anti-IL-4R antibody gradiently. 50 µl of a mixed solution of the anti-IL-4R antibody and IL-4 that was gradiently diluted with RPM1-1640 was added to the above 96-well plate. The 96-well plate was incubated in a 37° C. incubator for 2 days. After 2 days, the above cells were stained with PE Mouse Anti-Human CD23 fluorescently labeled antibody, and then fixed with 4% paraformaldehyde after staining, centrifuged at 300 g, washed, and subjected to fluorescence intensity detection of PE channel on a flow cytometer (CYTOMETER SYSTEM™, purchased from Beckman Coulter). FCS/SSC or CD14 fluorescent labeling intensity was used to determine the monocyte population and the software provided by the flow cytometer was used to process the experimental data and calculate the average fluorescence intensity. GRAPHPAD PRISM-6™ was used to analyze data, prepare graphs, and calculate IC50.

Figures 1, 10:
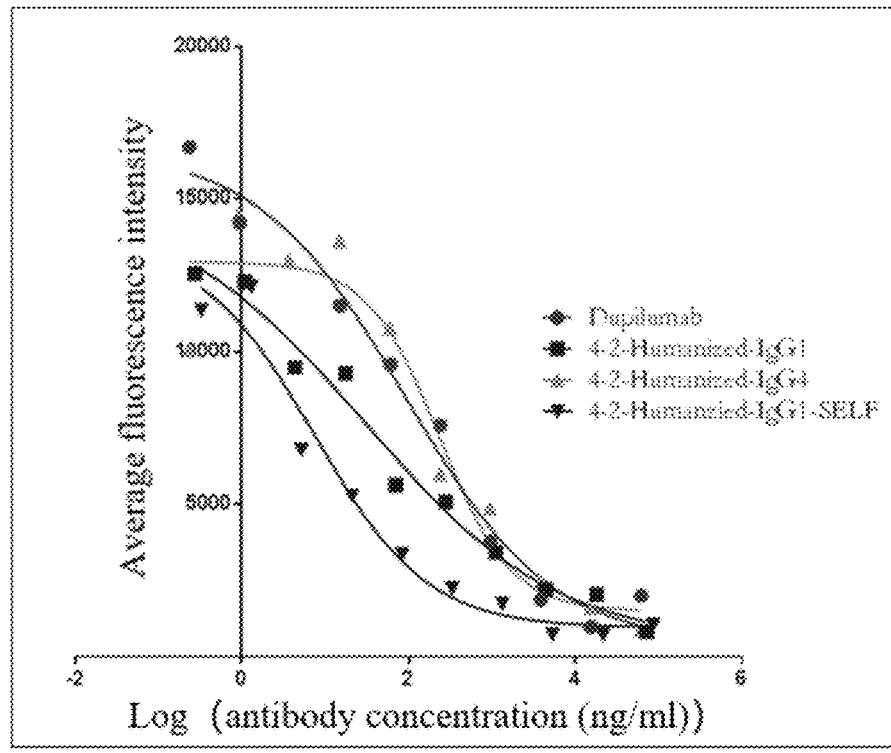
Figures 2, 10:
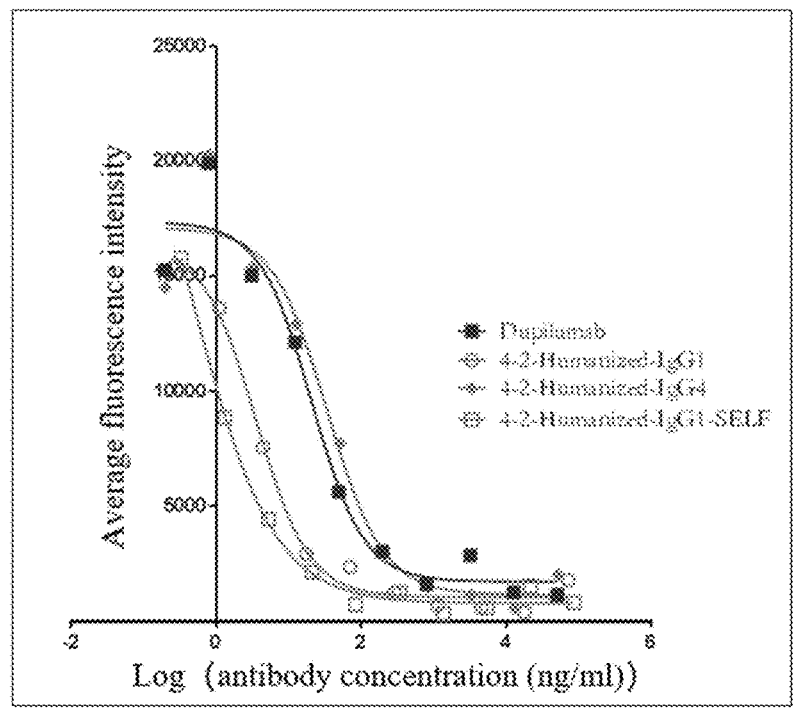
Figures 3, 10:
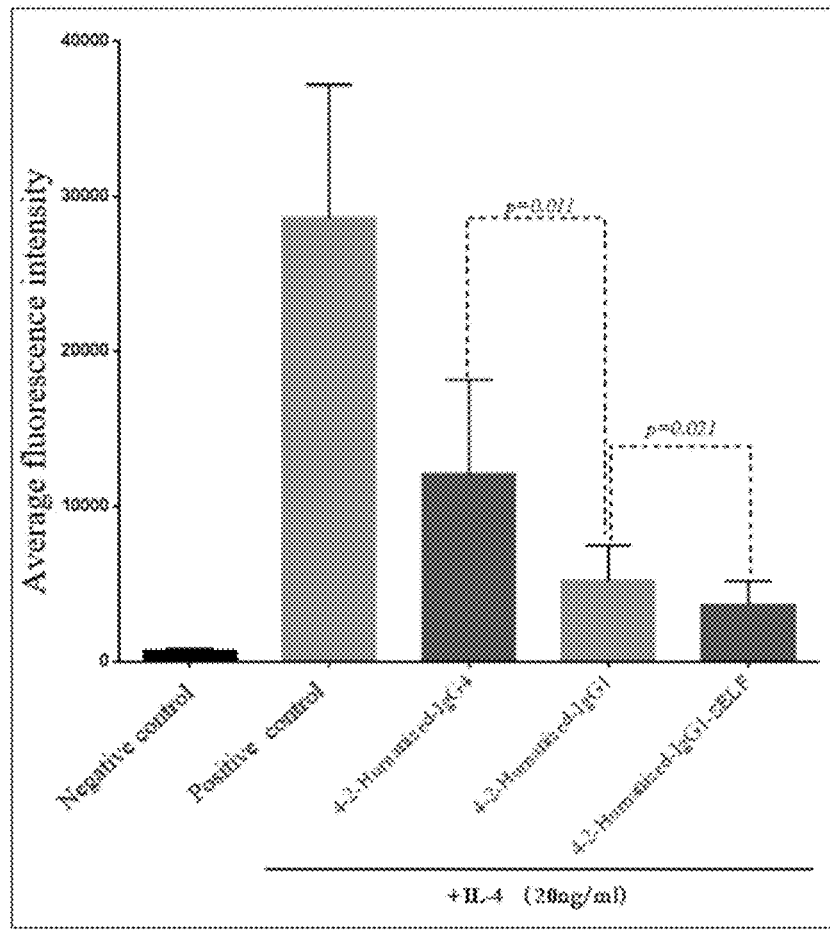

The results of the first experiment are shown in FIG. 10-1. Dupilumab, 4-2-Humanized-IgG1, 4-2-Humanized-IgG4 and 4-2-Humanized-IgG1-SELF can effectively inhibit IL-4-induced CD23 expression by PBMC, with an IC50 of 90.91 ng/ml., 29.38 ng/ml. 232.1 ng/ml and 7.404 ng/ml, respectively. The results of the second repeated experiment are shown in FIG. 10-2, the IC50s of Dupilumab, 4-2-Humanized-IgG1, 4-2-Humanized-IgG4 and 4-2-Humanized-IgG1-SELF for inhibition of IL-4-induced CD23 expression by PBMC were 20.65 ng/ml, 3.56 ng/ml, 34.00 ng/ml and 0.49 ng/ml, respectively. The functional activity intensity of the two independent repeated experiments was ranked as follows: 4-2-1-Humanized-IgG1-SELF>4-2-Humanized-IgG1>Dupilumab>4-2-Humanized-IgG4.
Wherein, the blood used in the two experiments was from different donors.

In order to further verify the above experimental results, PBMCs of 6 blood samples from different donors were separated using Histopaque and the cells were counted and then inoculated into a round-bottom 96-well cell culture plate using RMPI-1640 complete medium at 2E5 cells per well; anti-IL-4R antibody (final concentration of 25 ng/ml) and IL-4 (final concentration of 20 ng/ml) were then added and the 96-well plate was incubated in a 37° C. incubator for 2 days. After 2 days, the expression of CD23 was analyzed using a flow cytometer according to the above experimental method. Wherein, the negative control used did not contain IL-4 but contained a control antibody that does not bind to human IL-4R; the positive control contained IL-4 and a control antibody that does not bind to human IL-4R. The experimental results are shown in FIG. 10-3. The functional activity intensity of 4-2 antibodies was ranked as follows: 4-2-Humanized-IgG1-SELF>4-2-Humanized-IgG1>4-2-Humanized-IgG4, which had statistically significant difference (statistical method was T-test, P<0.05 was considered as statistically significant difference).

Example 6.4 Inhibitory Effects on IL-4-Induced IgE Secretion by PBMC

IL-4 can induce human peripheral blood mononuclear cells (PBMC) to secrete IgE molecules. IgE molecule is highly correlated with allergic reactions. In this example, PBMC was used to detect the inhibitory effects of 4-2-Humanized-IgG1, 4-2-Humanized-IgG4, and 4-2-Humanized-IgG1-SELF on IL-4-induced IgE secretion by PBMC.

PBMCs were separated from human whole blood using HISTOPAQUE™ and were counted and then inoculated into a round-bottom 96-well cell culture plate using RMPI-1640 complete medium (containing 10% fetal bovine serum) at 2E5 cells/150 µl per well. IL-4 was diluted to 80 ng/ml with RMPI-1640, and meanwhile, dexamethasone was added to a final concentration of 400 ng/ml, the obtained medium was used to dilute IL-4R antibody gradiently. 50 µl of a mixed solution of anti-IL-4R antibody, IL-4 and dexamethasone, which was gradiently diluted with RPMI-1640, was added to the above 96-well plate; the 96-well plate was incubated in a 37° C. incubator for 14 days. After 14 days, the cell culture supernatant was collected and tested for IgE secretion by the double-antibody sandwich method using Anti-Human IgE antibody as capture antibody and Biotin-anti-Human IgE antibody as detection antibody. GRAPHPAD PRISM-6™ was used to analyze data, prepare graphs, and calculate IC50.

Figures 1, 11:
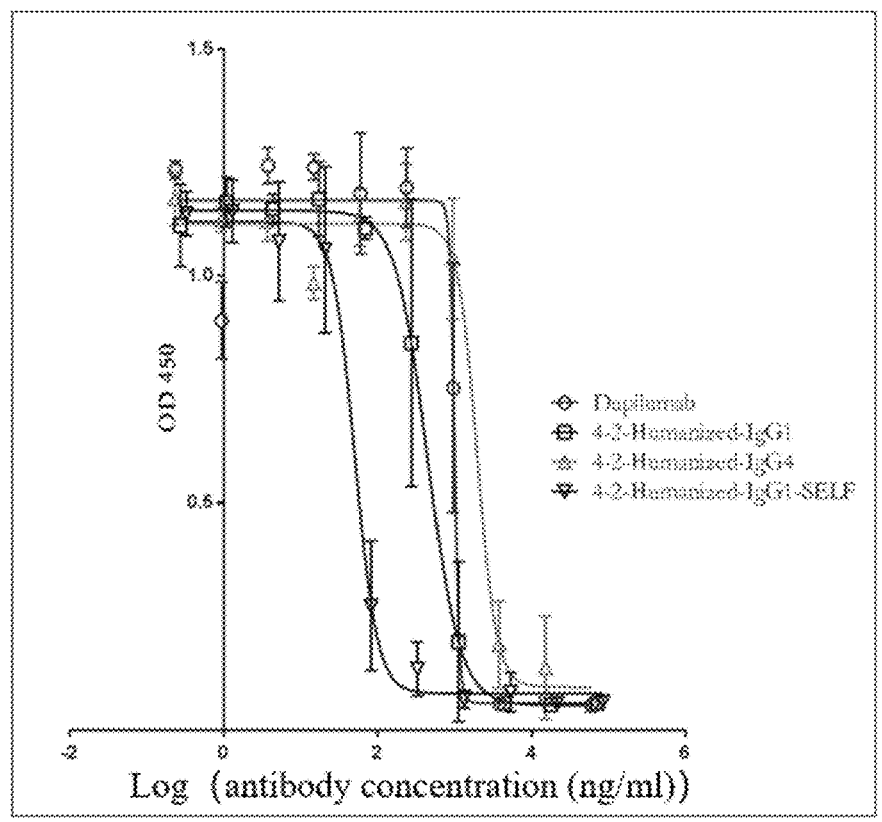
Figures 2, 11:
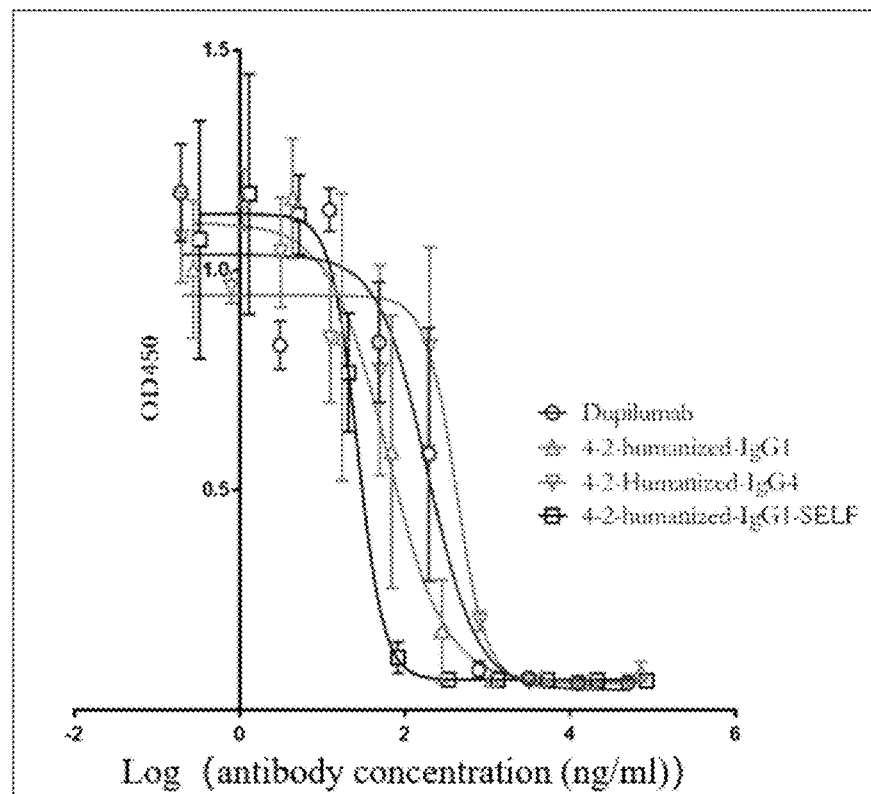

The results of the first experiment are shown in FIG. 11-1. Dupilumab, 4-2-Humanized-IgG1, 4-2-Humanized-IgG4 and 4-2-Humanized-IgG1-SELF can effectively inhibit IL-4-induced IgE secretion by PBMC, with IC50s of 995.7 ng/mil, 448.0 ng/ml, 1953 ng/ml and 50.85 ng/ml respectively. The results of the second repeated experiment are shown in FIG. 11-2. The IC50s of Dupilumab, 4-2-Humanized-IgG1, 4-2-Humanized-IgG4 and 4-2-Humanized-IgG1-SELF for inhibition of IL-4-induced IgE secretion by PBMC were 189.4 ng/ml, 61.34 ng/mi, 412.9 ng/ml and 26.61 ng/ml, respectively. The functional activity intensity in the two independent repeated experiments was ranked as follows: 4-2-Humanized-IgG1-SELF>4-2-Humanized-IgG1>Dupilumab>4-2-Humanized-IgG4. Wherein, the blood used in the two experiments was from different donors.

Example 7 Pharmacokinetic Study of Anti-Human IL-4R Humanized Antibody

In this example, the pharmacokinetics of 4-2-Humanized-IgG4 was detected by intravenous injection (I.V) into rats.

There were four rats in each group, weighing about 200 g. Each rat was intravenously injected with an anti-IL-4R monoclonal antibody at a dose of 1 mg. Blood was taken from the orbit at a specific time after administration. The blood was naturally coagulated and centrifuged to obtain serum. The determination method of antibody concentration in serum was as follows: An ELISA plate was coated with IL-4R-ECD-FLAG of a concentration of 100 ng/ml at 100 µl/well, blocked with PBST+1% BSA after the coating, and then added with a properly diluted rat serum. After a period of incubation, the plate was washed and finally added with HRP-labeled goat anti-human secondary antibody (purchased from Sigma; this antibody had been subjected to species cross-adsorption treatment and cannot recognize rat endogenous antibody). After another period of incubation, the plate was washed and added with a chromogenic solution for color development. The coloring reaction was stopped by a stop solution, and OD450 was determined. The OD450 was converted to an antibody concentration by a standard curve. GRAPHPAD PRISM-6™ was used to analyze data and prepare graphs and Phoenix software was used to calculate the half-life of the antibody drug in rats.

Figure 12:
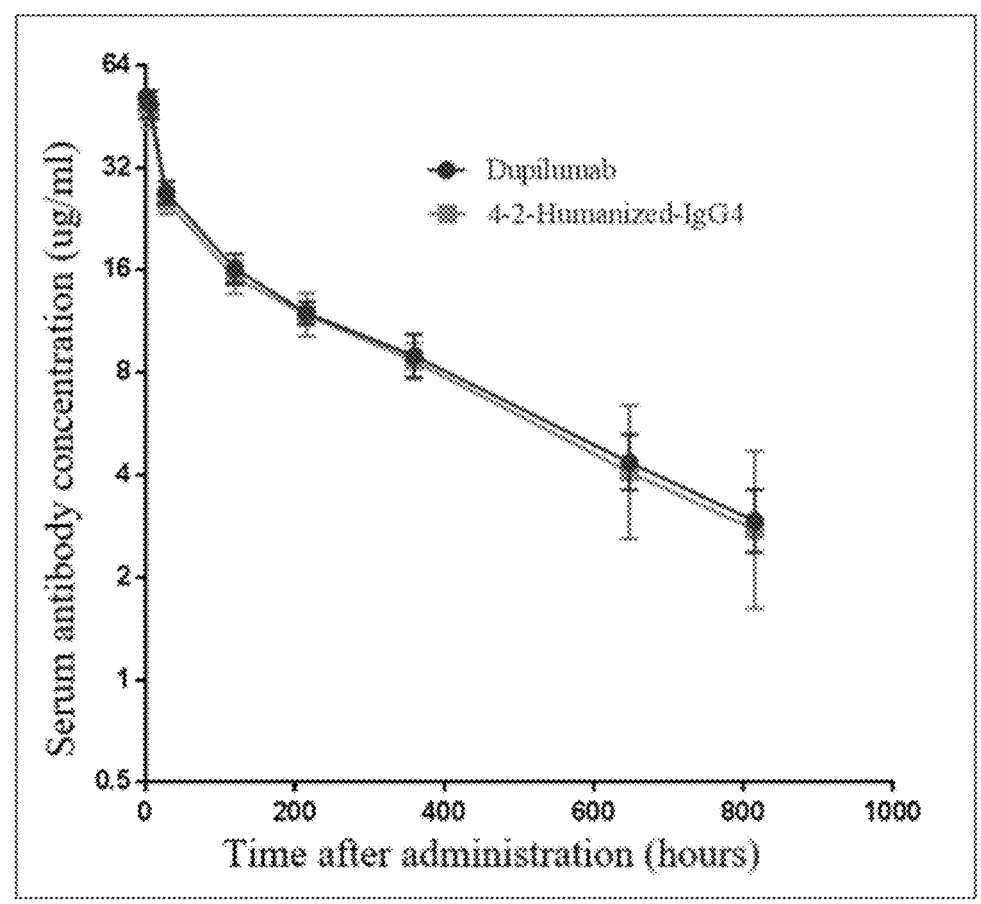
FIG. 12 shows the results of the pharmacokinetic study of 4-2-Humanized-IgG4.

As shown in FIG. 12, the pharmacokinetic results of intravenous injection showed that the half-life of the 4-2-Humanized-IgG4 antibody in rats was equivalent to that of the positive control antibody Dupilumab, which were 282.4 hours and 281.6 hours, respectively.

Example 8 Epitope Analysis of Anti-Human IL-4R Humanized Antibody

According to the literature (Zhang J L, Simeonowa 1, Wang Y, et al., The high-affinity interaction of human IL-4 and the receptor a chain is constituted by two independent binding clusters[J]. Journal of molecular biology, 2002, 315(3): 399-407), the amino acid residues that are located in the extracellular domain of IL-4Rα (amino acid sequence shown in SEQ ID NO: 1) and important for binding to IL-4 are as follows: F13, M14, S15, L39, F41, L42, L43, D66, D67, V68, D69, S70, D72, N73, Y74, K91, P92, S93, E94, D125, N126, Y127, L128, Y129 and Y183. In this example, site-directed mutagenesis was used to mutate each of the above-mentioned amino acid residues into alanine to construct a series of IL-4Rα mutants. The IL-4Rα mutants were expressed in HEK293E cells, respectively, and the corresponding mutants were purified by nickel affinity chromatography. The purified IL-4Rα mutants were used to coat ELISA plates (10 ng/well), and then ELISA was used to detect the bonding strength of 4-2-Humanized-IgG4 (4-2-Hu-IgG4) and Dupilumab to each of the IL-4Rα mutants. See Example 1.2 for the experimental method, except that IL-4R-ECD-hFc was replaced with the above IL-4Rα mutants, and the HRP-labeled goat anti-mouse secondary antibody was replaced with HRP-labeled goat anti-human secondary antibody. The results are shown in Table 2.

TABLE 2

Binding effects of 4-2-Hu-IgG4 and Dupilumab to IL-4Rα mutants

| Mutation site | 4-2-Hu-IgG4 | Dupilumab |
| --- | --- | --- |
| F13A | − | − |
| M14A | − | − |
| S15A | − | − |
| L39A | + | + |
| F41A | + | − |
| L42A | + | − |
| L43A | + | − |
| D66A | − | − |
| D67A | − | − |
| V68A | − | − |
| D69A | − | − |
| S70A | − | − |
| D72A | + | + |
| N73A | − | − |
| Y74A | + | + |
| K91A | − | − |
| P92A | − | − |
| S93A | − | − |
| E94A | − | − |
| D125A | − | − |
| N126A | − | − |
| Y127A | − | − |
| L128A | − | − |
| Y129A | − | − |
| Y183A | − | − |

Note: "+" indicates that the binding of the antibody to the mutant is significantly weaker (compared with wild-type IL-4Rα, the EC50 increased by more than three times); "−" indicates that the binding of the antibody to the mutant has no significant change (compared with wild-type IL-4Rα, the EC50 increased by no more than three times).

The experimental results showed that the binding effects of 4-2-Hu-IgG4 and Dupilumab to the three IL-4Rα mutants L39A. D72A, and Y74A were significantly weakened, indicating that the three amino acid residues L39, D72 and Y74 are necessary for 4-2-Hu-IgG4 and Dupilumab to effectively bind IL-4Rα; the binding effects of 4-2-Hu-IgG4 to the three IL-4Rα mutants of F41 A, L42A and L43A were significantly weaker but there was no obvious change in the binding effects of Dupilumab to the three IL-4Rα mutants, indicating that the three amino acid residues F41, L42 and L43 are necessary for 4-2-Hu-IgG4 to effectively bind IL-4Rα, but not necessary for Dupilumab to effectively bind IL-4Rα. The above results indicate that 4-2-Hu-IgG4 and Dupilumab have different epitopes.

The invention claimed is:

1. An antibody or antigen-binding fragment thereof that binds to human IL-4 receptor (IL-4R), wherein said antibody or antigen-binding fragment thereof comprises:
   (1) heavy chain complementarity determining regions HCDR1, HCDR2, HCDR3, wherein the HCDR1 having the amino acid sequence as shown in SEQ ID NO: 6, the HCDR2 having the amino acid sequence as shown in SEQ ID NO: 7, and the HCDR3 having the amino acid sequence as shown in SEQ ID NO: 8, and
   (2) light chain complementarity determining regions LCDR1, LCDR2, LCDR3, wherein the LCDR1 having the amino acid sequence as shown in SEQ ID NO: 9, the LCDR2 having the amino acid sequence as shown in SEQ ID NO: 10, and the LCDR3 having the amino acid sequence as shown in SEQ ID NO: 11.

2. The antibody or antigen-binding fragment thereof that binds to human IL-4R according to claim 1, wherein said antibody is a monoclonal antibody or a polyclonal antibody.

3. The antibody or antigen-binding fragment thereof that binds to human IL-4R according to claim 2, wherein said antibody is a monoclonal antibody.

4. The antibody or antigen-binding fragment thereof that binds to human IL-4R according to claim 1, wherein said antibody is a murine antibody, a chimeric antibody or a humanized antibody.

5. The antibody or antigen-binding fragment thereof that binds to human IL-4R according to claim 1, wherein said antibody is an IgG1 type antibody or an IgG4 type antibody.

6. The antibody or antigen-binding fragment thereof that binds to human IL-4R according to claim 1, wherein said antigen-binding fragment comprises a Fab fragment, a F(ab')2 fragment, a Fv fragment, a single chain antibody.

7. The antibody or antigen-binding fragment thereof that binds to human IL-4R according to claim 1, wherein said antibody or antigen-binding fragment thereof that binds to human IL-4R can block the interaction between IL-4 and IL-4R.

8. The antibody or antigen-binding fragment thereof that binds to human IL-4R according to claim 1, wherein said antibody or antigen-binding fragment thereof that binds to human IL-4R comprises a heavy chain variable region having the amino acid sequence as shown in SEQ ID NO: 3, and a light chain variable region having the amino acid sequence as shown in SEQ ID NO: 5; or said antibody or antigen-binding fragment thereof that binds to human IL-4R comprises a heavy chain variable region having the amino acid sequence as shown in SEQ ID NO:13, and a light chain variable region having the amino acid sequence as shown in SEQ ID NO:15.

9. The antibody or antigen-binding fragment thereof that binds to human IL-4R according to claim 8, wherein said antibody or antigen-binding fragment thereof that binds to human IL-4R comprises a heavy chain having the amino acid sequence as shown in SEQ ID NO:16, and a light chain having the amino acid sequence as shown in SEQ ID NO:18; or said antibody or antigen-binding fragment thereof that binds to human IL-4R comprises a heavy chain having the amino acid sequence as shown in SEQ ID NO:17, and a light chain having the amino acid sequence as shown in SEQ ID NO:18; or said antibody or antigen-binding fragment thereof that binds to human IL-4R comprises a heavy chain having the amino acid sequence as shown in SEQ ID NO:19, and a light chain having the amino acid sequence as shown in SEQ ID NO:18.

10. A pharmaceutical composition, wherein said pharmaceutical composition comprises an antibody or antigen-binding fragment thereof that binds to human IL-4 receptor (IL-4R) as set forth in claim 1, and a pharmaceutically acceptable carrier.

11. A method for treating a disease related to IL-4R overexpression comprising administering to an individual in need thereof a pharmaceutical composition according to claim 10.

12. The method according to claim 11, wherein said disease related to IL-4R overexpression is selected from the group consisting of atopic dermatitis, asthma, allergic reactions, eosinophilic esophagitis, skin infections, and nasal polyposis.

* * * * *

SEQUENCE LISTING

<160> NUMBER OF SEQ ID NOS: 20

<210> SEQ ID NO 1
<211> LENGTH: 207
<212> TYPE: PRT
<213> ORGANISM: Homo sapiens

<400> SEQUENCE: 1

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

```
Leu Arg Leu Leu Tyr Gln Leu Val Phe Leu Leu Ser Glu Ala His Thr
            35                  40                  45

Cys Ile Pro Glu Asn Asn Gly Gly Ala Gly Cys Val Cys His Leu Leu
 50                  55                  60

Met Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
            130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
            195                 200                 205

<210> SEQ ID NO 2
<211> LENGTH: 360
<212> TYPE: DNA
<213> ORGANISM: Mus musculus

<400> SEQUENCE: 2
caggtccaac tacagcagtc tggacctgag ctggtgaagc ctggggcttc agtgaagata      60
tcttgcacgg cttctggctc caccctcact gacgactata taaactgggt gaagcagagg     120
cctggacggg gacttgagtg ggttggatgg attttttcctg gaaatggtaa ttcttactac    180
aatgagaagt tcaaggacaa ggccacattg attgtagaca atcttccag cacagcctac      240 atgttgctca gcagcctgac ctctgaggac tctgcggtct atttctgtgc aagagggcta    300
gtacggtatc gcgccctttt tgactactgg ggccaaggca ccactctcac agtctcctca    360

<210> SEQ ID NO 3
<211> LENGTH: 120
<212> TYPE: PRT
<213> ORGANISM: Mus musculus

<400> SEQUENCE: 3

Gln Val Gln Leu Gln Gln Ser Gly Pro Glu Leu Val Lys Pro Gly Ala
 1               5                  10                  15

Ser Val Lys Ile Ser Cys Thr Ala Ser Gly Ser Thr Leu Thr Asp Asp
                20                  25                  30

Tyr Ile Asn Trp Val Lys Gln Arg Pro Gly Arg Gly Leu Glu Trp Val
            35                  40                  45

Gly Trp Ile Phe Pro Gly Asn Gly Asn Ser Tyr Tyr Asn Glu Lys Phe
 50                  55                  60

Lys Asp Lys Ala Thr Leu Ile Val Asp Lys Ser Ser Ser Thr Ala Tyr
 65                  70                  75                  80

Met Leu Leu Ser Ser Leu Thr Ser Glu Asp Ser Ala Val Tyr Phe Cys
                85                  90                  95
```

Ala Arg Gly Leu Val Arg Tyr Arg Ala Leu Phe Asp Tyr Trp Gly Gln
            100                 105                 110

Gly Thr Thr Leu Thr Val Ser Ser
        115                 120

<210> SEQ ID NO 4
<211> LENGTH: 318
<212> TYPE: DNA
<213> ORGANISM: Mus musculus

<400> SEQUENCE: 4
caaattgttc tctcccagtc tccagcaatc ctgtctgcat ctccagggga gaaggtcaca      60
atgacttgca gggccagctc aagtattaat tacatgcact ggtaccagca gaagccagga    120
tcctccccca aaccctggat ttatgccgca tccaacctgg cttctggagt ccctgctcgc    180
ttcagtggca gtgggtctgg gacctctttc tctctcacaa tcagcagagt ggaggctgaa    240
gatgctgcca cttattactg ccagcagtgg agtagttacc caatcacgtt cggctcgggg    300
acaaagttgg aaataaaa                                                  318

<210> SEQ ID NO 5
<211> LENGTH: 106
<212> TYPE: PRT
<213> ORGANISM: Mus musculus

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Ile Asn Tyr Met
            20                  25                  30

His Trp Tyr Gln Gln Lys Pro Gly Ser Ser Pro Lys Pro Trp Ile Tyr
        35                  40                  45

Ala Ala Ser Asn Leu Ala Ser Gly Val Pro Ala Arg Phe Ser Gly Ser
    50                  55                  60

Gly Ser Gly Thr Ser Phe Ser Leu Thr Ile Ser Arg Val Glu Ala Glu
65                  70                  75                  80

Asp Ala Ala Thr Tyr Tyr Cys Gln Gln Trp Ser Ser Tyr Pro Ile Thr
                85                  90                  95

Phe Gly Ser Gly Thr Lys Leu Glu Ile Lys
            100                 105

<210> SEQ ID NO 6
<211> LENGTH: 5
<212> TYPE: PRT
<213> ORGANISM: Mus musculus

<400> SEQUENCE: 6

Asp Asp Tyr Ile Asn
1               5

<210> SEQ ID NO 7
<211> LENGTH: 17
<212> TYPE: PRT
<213> ORGANISM: Mus musculus

<400> SEQUENCE: 7

Trp Ile Phe Pro Gly Asn Gly Asn Ser Tyr Tyr Asn Glu Lys Phe Lys
1               5                   10                  15

Asp

<210> SEQ ID NO 8
<211> LENGTH: 11
<212> TYPE: PRT
<213> ORGANISM: Mus musculus

<400> SEQUENCE: 8

Gly Leu Val Arg Tyr Arg Ala Leu Phe Asp Tyr
1               5                   10

<210> SEQ ID NO 9
<211> LENGTH: 10
<212> TYPE: PRT
<213> ORGANISM: Mus musculus

<400> SEQUENCE: 9

Arg Ala Ser Ser Ser Ile Asn Tyr Met His
1               5                   10

<210> SEQ ID NO 10
<211> LENGTH: 7
<212> TYPE: PRT
<213> ORGANISM: Mus musculus

<400> SEQUENCE: 10

Ala Ala Ser Asn Leu Ala Ser
1               5

<210> SEQ ID NO 11
<211> LENGTH: 9
<212> TYPE: PRT
<213> ORGANISM: Mus musculus

<400> SEQUENCE: 11

Gln Gln Trp Ser Ser Tyr Pro Ile Thr
1               5

<210> SEQ ID NO 12
<211> LENGTH: 360
<212> TYPE: DNA
<213> ORGANISM: Artificial Sequence
<220> FEATURE:
<223> OTHER INFORMATION: humanized heavy chain variable region

<400> SEQUENCE: 12
caggtgcagc tggtgcagtc cggagccgag gtgaaaaagc ccggcgcctc cgtgaaggtg      60
tcctgcaagg cctccggctc caccctgacc gacgactaca tcaactgggt gaggcaggct     120
cctggacaga ggctggagtg ggtgggctgg atcttccccg gcaacggcaa cagctactac     180
aacgagaagt tcaaggacag ggccaccctg accgtcgaca gtccgcctc caccgcctac      240 atggagctgt cctccctgag gtccgaggac accgccgtgt atttctgcgc tagggggctg     300
gtgaggtaca gggccctgtt cgactactgg ggccagggca ccctggtgac agtgtcctcc     360

<210> SEQ ID NO 13
<211> LENGTH: 120
<212> TYPE: PRT
<213> ORGANISM: Artificial Sequence
<220> FEATURE:
<223> OTHER INFORMATION: humanized heavy chain variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Leu Thr Asp Asp
            20                  25                  30

Tyr Ile Asn Trp Val Arg Gln Ala Pro Gly Gln Arg Leu Glu Trp Val
        35                  40                  45

Gly Trp Ile Phe Pro Gly Asn Gly Asn Ser Tyr Tyr Asn Glu Lys Phe
    50                  55                  60

Lys Asp Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Leu Val Arg Tyr Arg Ala Leu Phe Asp Tyr Trp Gly Gln
            100                 105                 110

Gly Thr Leu Val Thr Val Ser Ser
        115                 120

<210> SEQ ID NO 14
<211> LENGTH: 318
<212> TYPE: DNA
<213> ORGANISM: Artificial Sequence
<220> FEATURE:
<223> OTHER INFORMATION: humanized light chain variable region

<400> SEQUENCE: 14
gacatccaga tgacccagtc cccttcctcc ctgagcgctt ccgtgggcga cagggtgacc        60
atcacctgca gggcctcctc ctccatcaac tacatgcact ggtaccagca gaagcccggc       120
aaggctccca gccctggat ctacgccgcc tccaacctgg cctccggagt gccttccagg        180
ttttccggct ccggctccgg cacagacttc accctgacca tctcctccct gcagcccgag       240
gacttcgcca cctactactg ccagcagtgg tcctcctacc ccatcacctt cggccagggc       300
accaaggtgg agatcaag                                                     318

<210> SEQ ID NO 15
<211> LENGTH: 106
<212> TYPE: PRT
<213> ORGANISM: Artificial Sequence
<220> FEATURE:
<223> OTHER INFORMATION: humanized light chain variable region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Ile Asn Tyr Met
            20                  25                  30

His Trp Tyr Gln Gln Lys Pro Gly Lys Ala Pro Lys Pro Trp Ile Tyr
        35                  40                  45

Ala Ala Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Ile Thr
                85                  90                  95

Phe Gly Gln Gly Thr Lys Val Glu Ile Lys
            100                 105

-continued

```
<210> SEQ ID NO 16
<211> LENGTH: 450
<212> TYPE: PRT
<213> ORGANISM: Artificial Sequence
<220> FEATURE:
<223> OTHER INFORMATION: humanized IgG1 HC

<400> SEQUENCE: 16
```

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Leu Thr Asp Asp
            20                  25                  30

Tyr Ile Asn Trp Val Arg Gln Ala Pro Gly Gln Arg Leu Glu Trp Val
        35                  40                  45

Gly Trp Ile Phe Pro Gly Asn Gly Asn Ser Tyr Tyr Asn Glu Lys Phe
    50                  55                  60

Lys Asp Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Leu Val Arg Tyr Arg Ala Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 447
<212> TYPE: PRT
<213> ORGANISM: Artificial Sequence
<220> FEATURE:
<223> OTHER INFORMATION: humanized IgG4 HC

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Leu Thr Asp Asp
            20                  25                  30

Tyr Ile Asn Trp Val Arg Gln Ala Pro Gly Gln Arg Leu Glu Trp Val
        35                  40                  45

Gly Trp Ile Phe Pro Gly Asn Gly Asn Ser Tyr Tyr Asn Glu Lys Phe
    50                  55                  60

Lys Asp Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Leu Val Arg Tyr Arg Ala Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 18
<211> LENGTH: 213
<212> TYPE: PRT
<213> ORGANISM: Artificial Sequence
<220> FEATURE:
<223> OTHER INFORMATION: humanized LC

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Ile Asn Tyr Met
            20                  25                  30

His Trp Tyr Gln Gln Lys Pro Gly Lys Ala Pro Lys Pro Trp Ile Tyr
        35                  40                  45

Ala Ala Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205

Asn Arg Gly Glu Cys
    210

<210> SEQ ID NO 19
<211> LENGTH: 450
<212> TYPE: PRT
<213> ORGANISM: Artificial Sequence
<220> FEATURE:
<223> OTHER INFORMATION: humanized IgG1-SELF

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Leu Thr Asp Asp
            20                  25                  30

Tyr Ile Asn Trp Val Arg Gln Ala Pro Gly Gln Arg Leu Glu Trp Val
        35                  40                  45

Gly Trp Ile Phe Pro Gly Asn Gly Asn Ser Tyr Tyr Asn Glu Lys Phe
    50                  55                  60

Lys Asp Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Leu Val Arg Tyr Arg Ala Leu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Glu His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Phe Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 20
<211> LENGTH: 129
<212> TYPE: PRT
<213> ORGANISM: Homo sapiens

<400> SEQUENCE: 20

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
            115                 120                 125

Ser
```